(12) United States Patent
Crane et al.

(10) Patent No.: US 11,058,408 B2
(45) Date of Patent: *Jul. 13, 2021

(54) KNEE JOINT CAPSULAR DISRUPTION AND REPAIR

(71) Applicant: Arthrex, Inc., Naples, FL (US)

(72) Inventors: David Crane, Chesterfield, MO (US);
George Paletta, St. Louis, MO (US);
John Purcell, Chesterfield, MO (US);
Andrew Osika, Naples, FL (US);
Robert Harrison, Naples, FL (US)

(73) Assignee: ARTHREX, INC., Naples, FL (US)

( * ) Notice: Subject to any disclaimer, the term of this patent is extended or adjusted under 35 U.S.C. 154(b) by 357 days.

This patent is subject to a terminal disclaimer.

(21) Appl. No.: 16/116,503

(22) Filed: Aug. 29, 2018

(65) Prior Publication Data

US 2018/0360442 A1 Dec. 20, 2018

Related U.S. Application Data

(63) Continuation of application No. 15/662,631, filed on Jul. 28, 2017, now Pat. No. 10,076,321, which is a continuation of application No. 15/596,015, filed on May 16, 2017, now Pat. No. 10,085,738.

(60) Provisional application No. 62/470,473, filed on Mar. 13, 2017, provisional application No. 62/337,059, filed on May 16, 2016.

(51) Int. Cl.
| | |
|---|---|
| *A61B 17/04* | (2006.01) |
| *G09B 23/34* | (2006.01) |
| *A61B 17/00* | (2006.01) |
| *A61B 17/17* | (2006.01) |

(52) U.S. Cl.
CPC .... *A61B 17/0401* (2013.01); *A61B 17/00234* (2013.01); *A61B 17/1764* (2013.01); *G09B 23/34* (2013.01); *A61B 2017/0464* (2013.01)

(58) Field of Classification Search
CPC ........ A61B 17/0401; A61B 17/002341; A61B 17/17654; A61B 2017/0409; A61B 2017/0464; G09B 23/30; G09B 23/32; G09B 23/34
See application file for complete search history.

(56) References Cited

U.S. PATENT DOCUMENTS

| | | |
|---|---|---|
| 4,433,961 A | 2/1984 | Chandler |
| 4,850,877 A | 7/1989 | Mason |
| 5,967,790 A | 10/1999 | Stover |

(Continued)

FOREIGN PATENT DOCUMENTS

| | | |
|---|---|---|
| DE | 202011002311 U1 | 3/2012 |
| WO | 2018213417 A1 | 11/2018 |

OTHER PUBLICATIONS

International Report on Patentability for corresponding PCT application No. PCT/US2017/032799 dated Nov. 29, 2018.

(Continued)

*Primary Examiner* — Diane D Yabut
(74) *Attorney, Agent, or Firm* — DLA Piper LLP US

(57) ABSTRACT

Meniscal extrusion can occur due detachment of the knee capsule from structures of the knee. Disclosed herein are methods to repair the meniscal detachment. Additionally, cadaveric and synthetic models can be used to teach said methods of repair.

14 Claims, 10 Drawing Sheets

(56) References Cited

U.S. PATENT DOCUMENTS

| | | | |
|---|---|---|---|
| 6,361,729 B1 * | 3/2002 | Strover | G09B 23/285 264/247 |
| 7,029,477 B2 | 4/2006 | Grimm | |
| 7,591,850 B2 | 9/2009 | Cavazzoni | |
| 7,686,838 B2 | 3/2010 | Wolf | |
| 7,931,655 B2 | 4/2011 | Axelson | |
| 8,226,726 B2 | 7/2012 | Abendschein | |
| 8,439,926 B2 | 5/2013 | Bojarski | |
| 8,444,968 B2 | 5/2013 | Seyedin | |
| 9,084,618 B2 | 7/2015 | Serbousek | |
| 9,138,219 B2 | 9/2015 | Horrell | |
| 9,433,425 B2 | 9/2016 | Wilkinson | |
| 9,636,100 B2 | 5/2017 | Wyman | |
| 9,655,609 B2 | 5/2017 | Rizk | |
| 9,855,062 B2 | 1/2018 | Blum | |
| 9,867,709 B2 | 1/2018 | Nocco | |
| 9,955,980 B2 | 5/2018 | Norton | |
| 9,974,550 B2 | 5/2018 | Seitlinger | |
| 10,028,751 B2 | 7/2018 | Blank | |
| 10,070,964 B2 | 9/2018 | Clifford | |
| 10,172,607 B2 | 1/2019 | Burkhart | |
| 2004/0059416 A1 | 3/2004 | Murray | |
| 2010/0010497 A1 | 1/2010 | Goble | |
| 2010/0136510 A1 | 6/2010 | Sakezles | |
| 2011/0022084 A1 | 1/2011 | Sengun | |
| 2014/0135926 A1 | 5/2014 | Forsell | |
| 2015/0018881 A1 | 1/2015 | Cauldwell | |
| 2015/0039030 A1 | 2/2015 | Saliman | |
| 2017/0162078 A1 | 6/2017 | Imhauser | |
| 2018/0021035 A1 | 1/2018 | Bourque | |
| 2018/0055507 A1 | 3/2018 | Bachmaier | |
| 2018/0125668 A1 | 5/2018 | Nocco | |
| 2018/0199931 A1 | 7/2018 | Saliman | |
| 2018/0199952 A1 | 7/2018 | Cole | |
| 2018/0280018 A1 | 10/2018 | Laprade | |
| 2019/0000660 A1 | 1/2019 | Emmerling | |

OTHER PUBLICATIONS

Office Action, issued in Japanese Application No. 2018-560188, dated Dec. 4, 2019, 8 pages.

De Maeseneer et al., "three Layers of the Medical Capsular and Supporting Structures of the Knee: MR Imaging—Anatomic Correlation", RadioGraphics, 20:S83-S89 (2000).

Coronary ligament of the knee, Wikipedia (https://en.wikipedia.org/wiki/Coronary_ligament_of_the_knee), 2 pages, printed from the World Wide Web on Apr. 26, 2017.

"Invitation to Pay Additional Fees, and Where Applicable, Protest Fee", prepared by International Searching Authority (EPO), dated Jul. 25, 2017, issued in connection with International Application No. PCT/US2017/032799, filed on May 16, 2017, 11 pages.

Drakonaki et al, "Ultrasound elastography for musculoskeletal applications", The British Journal of Radiology, vol. 85, pp. 1435-1445, (2012).

Examination Communication in EP Application No. 17726074.2 dated Feb. 27, 2020, 6 pages.

\* cited by examiner

KNEE JOINT CAPSULAR DISRUPTION AND REPAIR

CROSS-REFERENCE TO RELATED APPLICATIONS

This application is a continuation of U.S. patent application Ser. No. 15/662,631, Jul. 28, 2017, now U.S. Pat. No. 10,076,321, which is a continuation of U.S. patent application Ser. No. 15/596,015, filed May 16, 2017, now U.S. Pat. No. 10,085,738, which claims priority under 35 U.S.C. § 119(e) to U.S. Provisional Patent Application Ser. No. 62/337,059, filed on May 16, 2016, and entitled "Meniscal Capsular Disruption and Repair," and to U.S. Provisional Patent Application Ser. No. 62/470,473, filed on Mar. 13, 2017, and entitled "Knee Joint Capsular Disruption And Repair." The full disclosures of U.S. patent application Ser. No. 15/662,631, U.S. patent application Ser. No. 15/596,015, U.S. Provisional Patent Application Ser. No. 62/337,059, and U.S. Provisional Patent Application Ser. No. 62/470,473 are incorporated herein by reference in their entireties.

BACKGROUND

The disclosure herein describes methods of treating extrusion of the meniscus, which can possibly delay the early onset of osteoarthritis, further meniscal damage, and meniscal root pathology.

The meniscus is a crescent-shaped cartilage pad that functions to cushion and stabilize the knee joint. In particular, the meniscus acts as a shock absorber between the femur and the tibia. A common knee injury is meniscal extrusion, which occurs when the meniscus drifts from its anatomical position in the knee. When the meniscus is in an extruded position, there is reduced function of the meniscus in cushioning and stabilizing the knee joint. Meniscal extrusion is often associated with meniscal degeneration, a meniscal tear (e.g., a radial tear, a longitudinal tear, or an oblique tear), a torn meniscal root, and/or osteophyte formation.

Current methods of treating a meniscal extrusion include both non-surgical treatment and surgical repair. Non-surgical treatment is often attempted prior to surgical repair, and example non-surgical treatment includes physical therapy and/or insertion of biologics to facilitate the healing of the meniscus. However, in the event that non-surgical treatment is not successful in treating the meniscal extrusion, surgical repair can be performed to treat the meniscal extrusion. Surgical repair is usually performed arthroscopically, and a knee arthroscopy to treat the meniscus typically includes repairing any meniscal tear(s) and/or repairing a torn meniscal root. Knee arthroscopy can also include removal of osteophytes that have formed.

Current surgical repair methods for treating a meniscal extrusion have various drawbacks. For example, current methods do not treat the underlying injury that results in a meniscal extrusion. The meniscus drifts due to a disruption in the capsule of the knee, whereby the capsule becomes detached from at least one structure of the knee joint (e.g., the meniscus, tibial periosteum, femoral periosteum, etc.) and/or the meniscotibial ligament (MCL) detaches from its insertion point. Capsular disruption can occur concomitantly with a meniscal root tear. Alternatively, capsular disruption can occur, followed by meniscal extrusion, which then leads to a meniscal root tear. Current methods for treating a meniscal extrusion do not adequately address or treat the capsular disruption. Since current surgical repair methods do not treat this capsular disruption, the underlying injury that results in the meniscal extrusion remains after current surgical repair methods. Thus, surgical repair methods, and symptom relief, may only be temporary since the underlying injury remains. After time, the surgically repaired meniscus can begin to extrude again.

Improved systems and methods for repairing a meniscal extrusion are needed. In particular, systems and methods that treat the underlying injury that results in a meniscal extrusion are needed. Systems and methods for teaching improved systems and methods for repairing a meniscal extrusion are also needed.

SUMMARY

A capsular disruption can result in meniscal extrusion, which occurs when the meniscus drifts from its anatomical position in the knee. The meniscus drifts medially or laterally ("extruding" from the knee joint). The meniscus drifts due to a disruption in the capsule of the knee, whereby the capsule becomes detached from at least one structure of the knee joint (e.g., the meniscus, tibial periosteum, femoral periosteum, etc.) and/or the meniscotibial ligament detaches from its insertion point. The capsule can develop laxity and/or tears through degeneration or trauma to the three layer structure of the medial and/or lateral capsule. Additionally or alternatively, the capsule can develop laxity and/or tears through degeneration or trauma to the meniscotibial fibers of the meniscotibial ligament. Capsular disruption can occur concomitantly with a meniscal root tear. Alternatively, capsular disruption can occur, followed by meniscal extrusion, which then leads to a meniscal root tear. A meniscal root tear is often associated with the subsequent short or long term development of osteoarthritis.

As a particular example of capsular disruption resulting in meniscal extrusion, the medial inferior knee capsule can begin peeling away from the tibia, and this peeling away can lead to meniscal extrusion. The medial inferior knee capsule can peel away from the tibia for various reasons, such as trauma and/or degeneration. In an example, the trauma and/or degeneration causes coronary fibers of the meniscotibial ligament to detach from the tibia. When the medial inferior knee capsule peels away from the tibia, the meniscus loses a portion of support, and the anterior horn of the medial meniscus can incur further trauma. This further trauma leads to a disruption of this attachment point of the meniscus, allowing the meniscus to extrude to a greater distance. When the meniscus is in the extruded position, there is reduced function of the meniscus in cushioning and stabilizing the knee joint. Continued micro-motion of meniscus extrusion can further progress the disruption of the capsule from the tibia. As the meniscus further extrudes, the posterior horn of the meniscus can become avulsed.

Although the above example describes a progressive extrusion from the anterior to the posterior aspect of the knee, other example progressions are possible as well. For instance, it is also possible that a traumatic event or degeneration can cause a disruption to the posterior horn of the medial meniscus, thereby leading to the progressive extrusion of the meniscus from the posterior to anterior aspect of the knee. Additionally, although the above example describes a capsular disruption of the medial inferior knee capsule, in other examples the lateral knee capsule peels away from the tibia. Furthermore, although the above examples describe the knee capsule peeling away from the tibia, the knee capsule can peel away from other structures of the knee joint. For instance, in other examples, the knee capsule peels away from the femur.

Disclosed herein are methods of repairing a capsular disruption to re-attach the capsule to a knee structure. A repair of capsular disruption can be performed concomitantly with a meniscal root repair. If the meniscal root is not torn, the capsular disruption can be repaired so the meniscus does not extrude further, and the condition does not progress to a torn meniscal root. An embodiment includes inserting one or more anchors through the capsule. The anchor can be inserted into a knee joint structure to re-attach the capsule to that structure.

The methods and systems in accordance with the present disclosure beneficially provide improved methods and systems for repairing a meniscal extrusion. In particular, the disclosed methods and systems treat the underlying injury of capsular disruption that leads to a meniscal extrusion. By treating this underlying injury, the disclosed methods and systems of repairing a meniscal extrusion result in a more effective repair of the meniscal extrusion compared to existing repairs of meniscal extrusions. Furthermore, in accordance with example embodiments, the disclosed methods and systems also provide improved methods and systems for teaching and/or practicing repair of a meniscal extrusion.

In an example in accordance with the present disclosure, methods of repairing capsular disruption are described. The methods include inserting one or more anchors through a knee joint capsule of a knee. The method further includes inserting the one or more anchors into a knee joint structure to secure the knee joint capsule to the knee joint structure.

In another example in accordance with the present disclosure, methods of creating a capsular disruption are described. A method includes placing an instrument between a knee joint capsule of a knee and a knee joint structure of the knee. A method then includes disrupting the attachment of the knee joint capsule from the knee joint structure by physically elevating the instrument to force a capsular disruption. In an embodiment, the instrument has a flat surface (e.g., a banana blade) so soft tissue is not cut when the instrument is elevated.

In another example in accordance with the present disclosure, methods to teach or practice repairing meniscal extrusion are described. A method includes using a cadaveric knee to teach or practice a method of repairing a capsular disruption, wherein said method comprises (i) inserting one or more anchors through the knee joint capsule and (ii) inserting the one or more anchors into the knee joint structure to secure the knee joint capsule to the knee joint structure. In another embodiment, a cadaveric knee is used to teach repairing a meniscal tear in combination with repairing a capsular disruption.

In another example in accordance with the present disclosure, a method to teach or practice repairing a meniscal extrusion is described. The method includes using a synthetic knee to teach or practice repairing the meniscal extrusion, wherein the synthetic knee comprises a synthetic knee joint capsule and a synthetic knee joint structure. Using a synthetic knee to teach or practice repairing the meniscal extrusion includes (i) inserting one or more anchors through a synthetic knee joint capsule of a synthetic knee and (ii) inserting the one or more anchors into a synthetic knee joint structure to repair a capsular disruption by securing the synthetic knee joint capsule to the synthetic knee joint structure.

In another example in accordance with the present disclosure, a knee model is described. The knee model includes at least part of a tibia, at least part of a femur, a detachable meniscus, a detachable knee capsule, and a detachable meniscotibial ligament, wherein all of the components are synthetic.

The features, functions, and advantages that have been discussed can be achieved independently in various embodiments or can be combined in yet other embodiments further details of which can be seen with reference to the following description and drawings.

DETAILED DESCRIPTION

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein.

A method of repairing a capsular disruption to re-attach the capsule to a structure is disclosed herein. Meniscal extrusion can occur when there is capsular disruption, i.e., detachment or tearing of the knee capsule from at least one structure of the knee joint. In an embodiment, a capsular disruption tear can be less than 0.5 mm, about 0.5 mm, about 1 mm, about 2 mm, about 3 mm, about 4 mm, about 5 mm, about 6 mm, about 7 mm, about 8 mm, about 9 mm, about 10 mm, or about more than 10 mm. Medial or lateral drift of the meniscus (i.e., meniscal extrusion) can be about 5%, about 10%, about 15%, about 20%, about 25%, about 30%, about 35%, about 40%, about 45%, about 50%, about 55%, about 60%, about 65%, about 70%, about 75%, or about more than 75%. In an embodiment, injuries can be graded according to the length of the tear in combination with the percent extrusion. For example, a Grade 1 injury occurs when there is minimal capsular disruption with a 10% or less meniscal extrusion. A Grade 2 injury occurs when there is a 3 mm or less tear with a 25% or less meniscal extrusion. A Grade 3 injury occurs when there is an 8 mm or less tear with a 50% or less meniscal extrusion. A Grade 4 injury occurs when there is an 8 mm or more tear with a 50% or more meniscal extrusion. Other meniscal-injury grading scales can be used as well and may change over time with greater research after recognition of the underlying injury.

Figure 1:
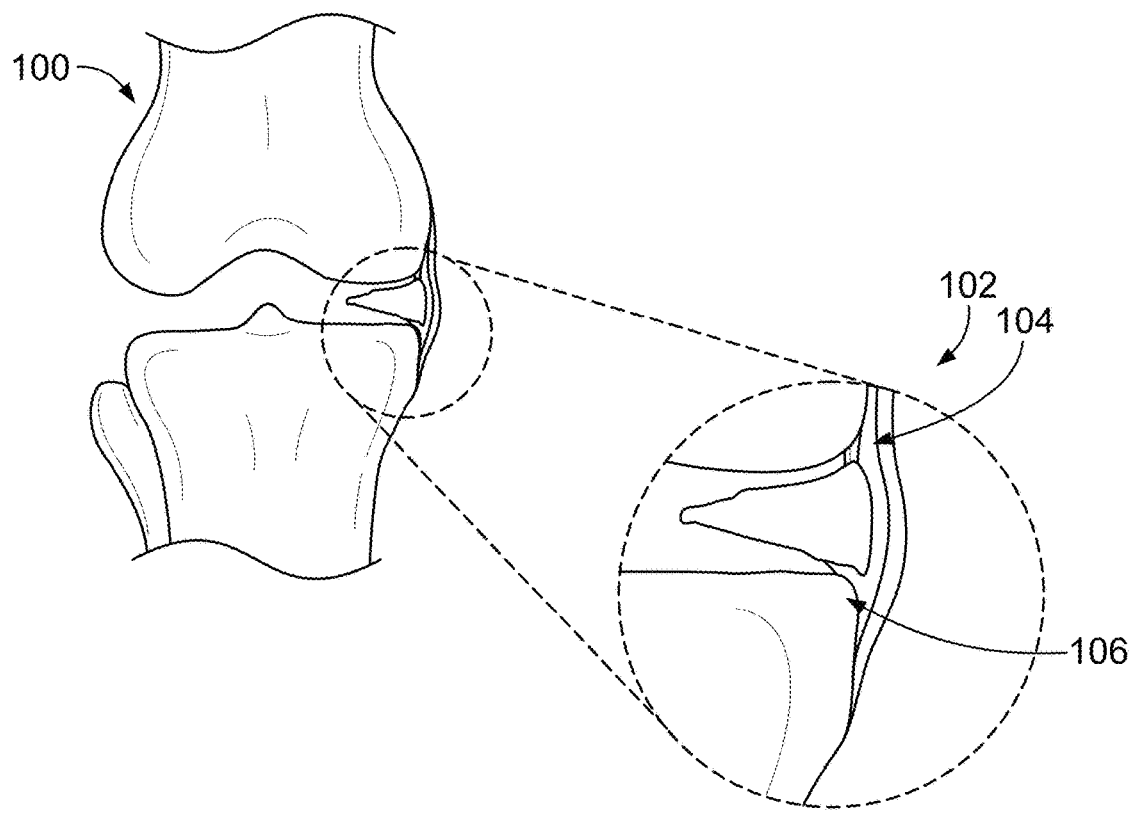
FIG. 1 illustrates an example meniscal extrusion, according to an example embodiment.

FIGS. 1-4 illustrate various example meniscal extrusions. In particular, FIG. 1 illustrates a knee 100 having an example Grade I injury 102. In this example, there is a 10% or less meniscal extrusion 104. In this example injury 102, there is also a sprain with edema in the tissue or associated marrow attachment of the meniscotibial ligament 106. Furthermore, in this example injury 102, there is no medial collateral ligament (MCL) sprain or involvement other than edema, and there are no or minimal osteophytes present.

Figure 2:
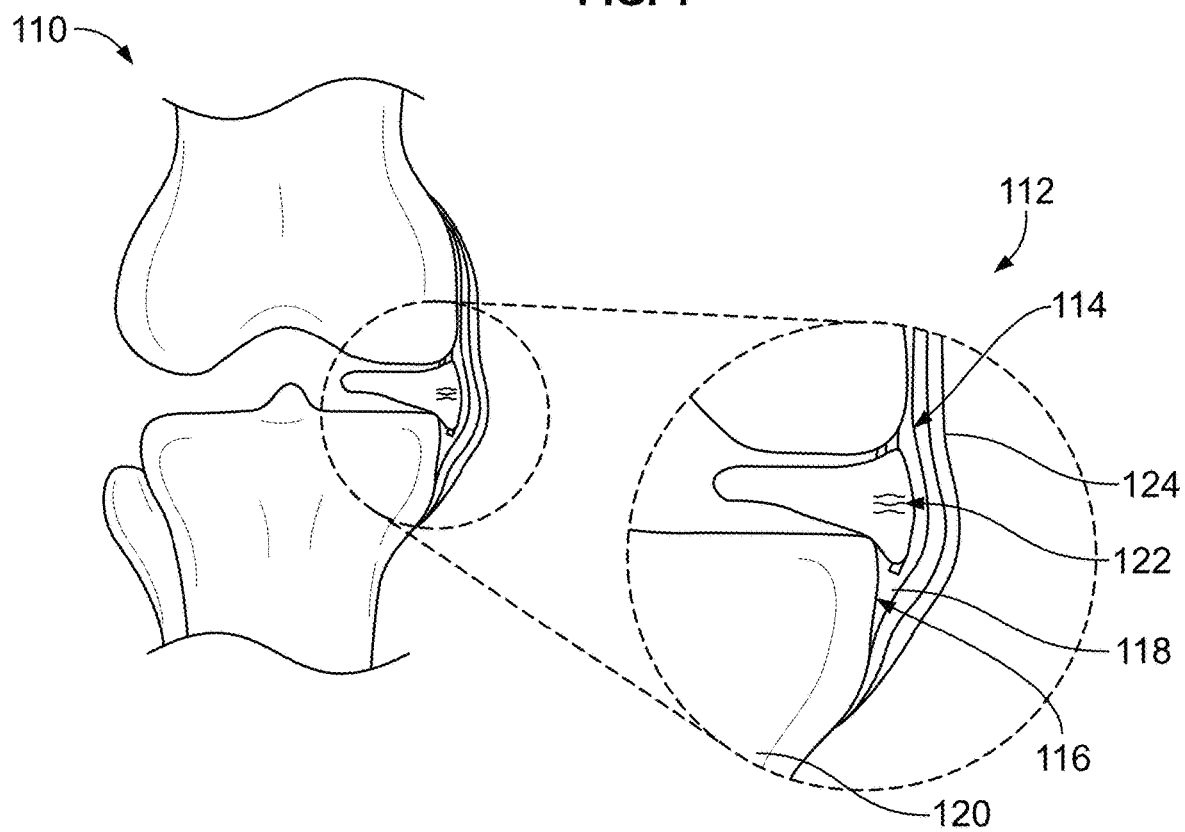
FIG. 2 illustrates an example meniscal extrusion, according to an example embodiment.

FIG. 2 illustrates a knee 110 having an example Grade II injury 112. In this example, there is a 25% or less meniscal extrusion 114. There is also a 3 mm or less capsule disruption tear 116 in which the capsule 118 is separated from the tibia 120. Furthermore, in this example, there can be mild degeneration, such a minimal meniscal degeneration or cleavage tear. For instance, FIG. 2 shows mild degeneration 122. In this example injury 112, there is also a mild sprain of the MCL 124, and there are no or minimal osteophytes present. The meniscal extrusion 114 is reducible with compartment dynamic off-loading.

Figure 3:
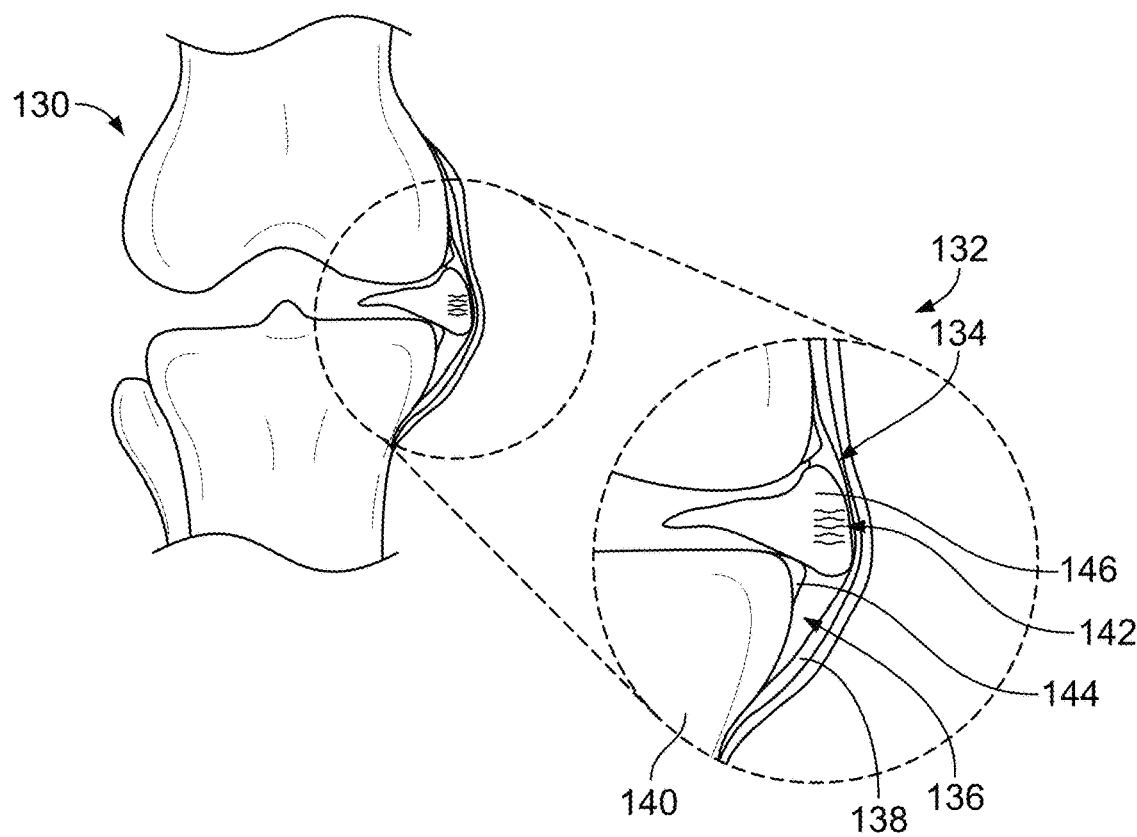
FIG. 3 illustrates an example meniscal extrusion, according to an example embodiment.

FIG. 3 illustrates a knee 130 having an example Grade III injury 132. In this example, there is a meniscal extrusion 134 of approximately 25-50%. There is also a 8 mm or less capsule disruption tear 136 in which the capsule 138 is separated from the tibia 140. Furthermore, in this example there can be moderate meniscal degeneration and/or osteophyte formation. For instance, FIG. 3 shows moderate degeneration 142 and osteophyte 144. In this example, the meniscal extrusion 134 is reducible with compartment dynamic off-loading. However, due the osteophyte formation, the meniscus 146 may or may not be fully reducible.

Figure 4:
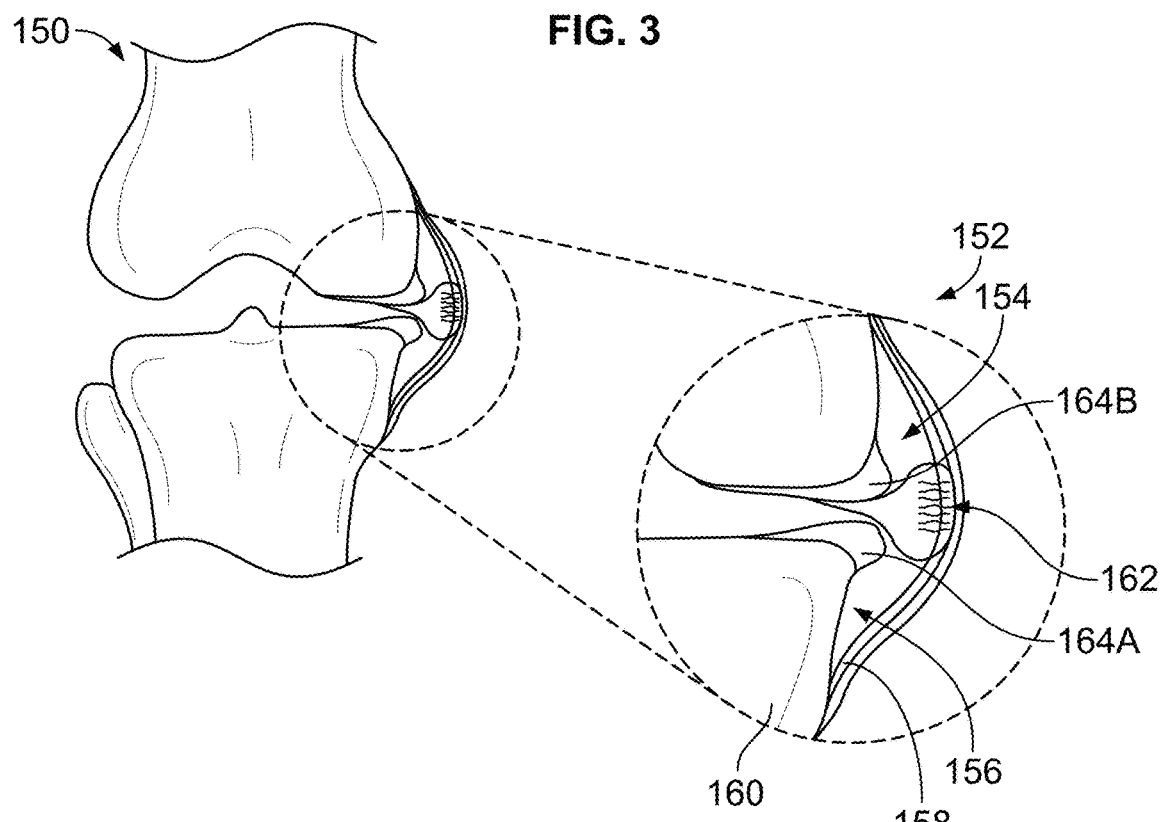
FIG. 4 illustrates an example meniscal extrusion, according to an example embodiment.

FIG. 4 illustrates a knee 150 having an example Grade IV injury 152. In this example, there is a meniscal extrusion 154 of approximately 50% or more. There is also a 8 mm or less capsule disruption tear 156 in which the capsule 158 is separated from the tibia 160. Furthermore, in this example there can be severe meniscal degeneration or tearing with osteophytes present. For instance, FIG. 4 shows severe degeneration 162 and osteophytes 164a-b. In this example, the meniscal extrusion 154 is not substantially reducible with compartment dynamic off-loading.

Disclosed herein are methods of repairing a capsular disruption that produce meniscal extrusions as shown in FIGS. 1-4. An example method of repair includes inserting one or more anchors through the capsule. The anchor can be inserted into a knee joint structure to re-attach the capsule to that structure. Any suitable anchors are possible. For instance, in an example embodiment, the anchor is a suture anchor (knotless or knotted; e.g., a SutureTak® anchor, Quattro® Link knotless anchors, Twinfix® anchors, Bioraptor® anchors, Spyromite® anchors, Dynomite® anchors, Osteoraptor® anchors, Raptomite® anchors, JuggerKnot® anchors, JuggerKnotless® anchors, etc.), a soft tissue anchor (e.g., Eclipse™ soft tissue anchor, Piton™ soft tissue fixation implant, etc.), or the like. In another example, the anchor is a staple. Other anchors are possible as well.

In an example embodiment, a method for repairing a capsular disruption is performed to repair a capsular disruption before a meniscal extrusion has occurred. In another example, the method for repairing a capsular disruption is performed to repair a capsular disruption that resulted in an associated meniscal extrusion. For instance, the method for repairing a capsular disruption could be used to repair the capsular disruptions resulting in meniscal extrusions shown in FIGS. 1-4.

An example method can involve positioning an arthroscope in a position to allow visualization of the knee joint capsule and the knee joint structure. The example method can involve placing a spinal needle through the skin into the knee joint space to mark an area above the meniscus. The example method can involve visualizing the spinal needle with the arthroscope to identify a location for inserting one or more anchors through the knee joint capsule. The example method can involve, for each anchor of the one or more anchors, drilling a socket in the bone for inserting the anchor into the bone. The method can involve inserting the one or more anchors through the knee joint capsule of a knee. The example method can involve inserting the one or more anchors into the drilled socket to secure the knee joint capsule to the knee joint structure. The example method can involve securing flexible strands (e.g., suture, suture tape, etc.) from one anchor to another anchor.

Figure 5:
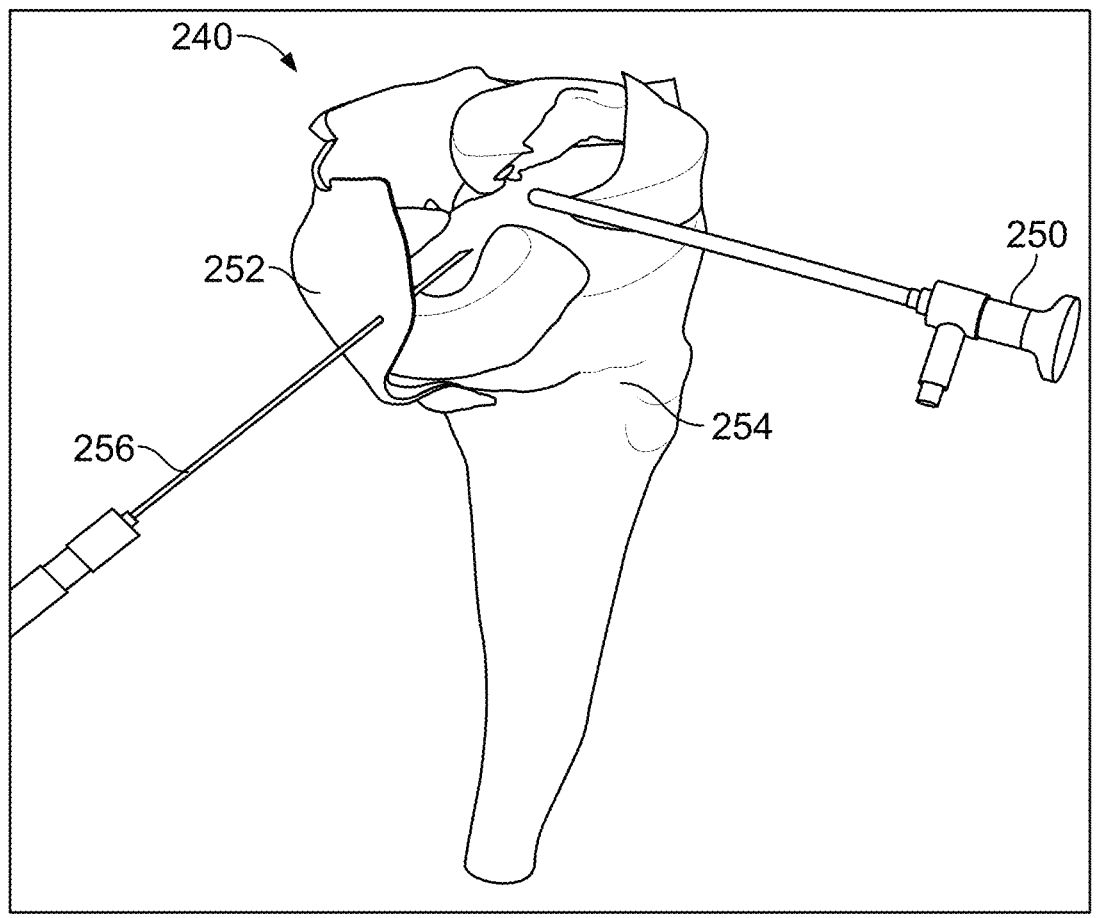
FIGS. 5-14 illustrate various example steps of repairing at least one of a capsular disruption or a meniscal extrusion, according to an example embodiment.

This example method is described in further detail with reference to FIGS. 5-14. FIG. 5 illustrates a knee 240 upon which the example method is performed. In this example, knee 240 is illustrated as a synthetic knee model. However, in other examples, the knee 240 is a knee of a patient. In yet other examples, the knee 240 is a cadaveric knee.

The knee 240 includes a knee joint capsule 252 and a knee joint structure 254. As seen in FIG. 5, the example method involves positioning an arthroscope 250 in a position to allow visualization of the knee joint capsule 252 and the knee joint structure 254. The example method also involves placing a spinal needle 256 through the skin (not shown) into the knee joint space. Furthermore, the example method involves visualizing the spinal needle 256 with the arthroscope 250 to identify a location for inserting one or more anchors through the knee joint capsule 252.

In the example of FIGS. 5-14, the area of the knee joint capsule 252 through which the one or more anchors are inserted is the medial capsule. However, in other example embodiments, an area of the knee joint capsule 252 through which the one or more anchors are inserted is the lateral capsule. Furthermore, in the example embodiment of FIGS. 5-14, the knee joint structure 254 into which the one or more anchors are inserted is the tibia. However, in other example embodiments, the knee joint structure 254 is the femur.

Figure 6:
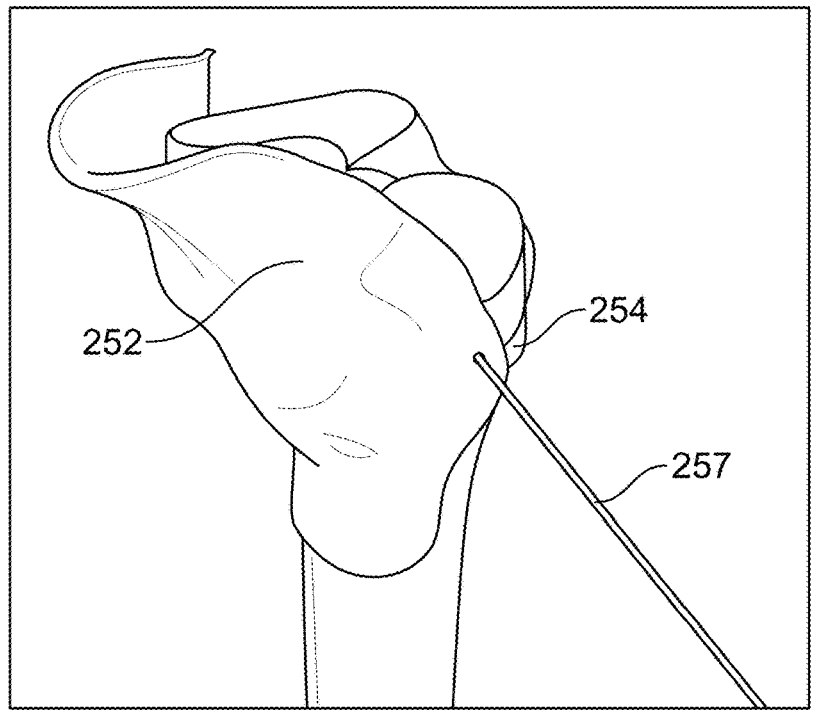
Figure 7:
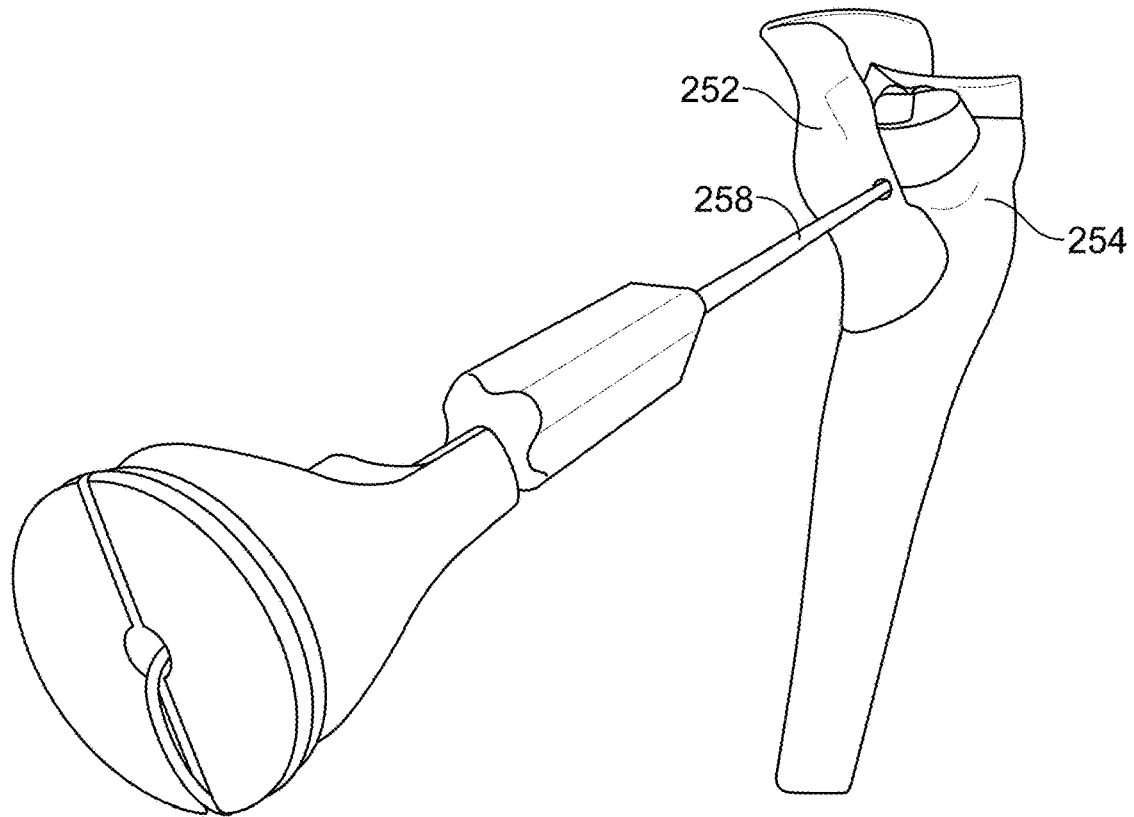
Figure 8:
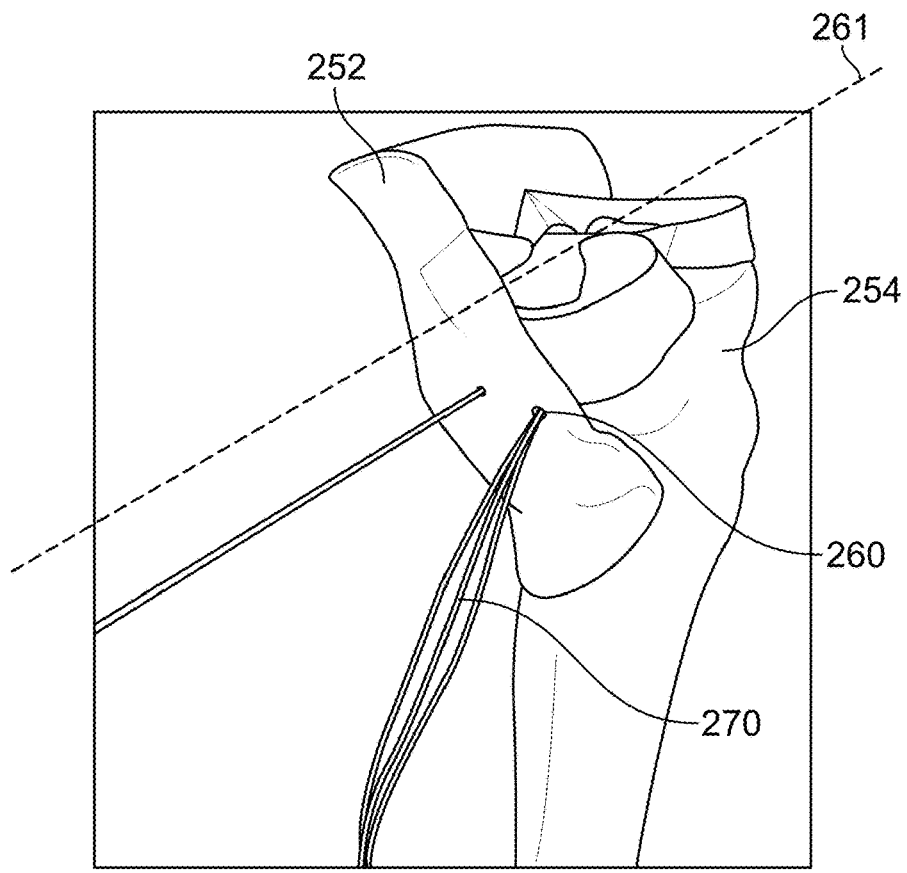

In the illustrated example, the one or more anchors include a first anchor and a second anchor. FIGS. 5-7 illustrate identification of the location for inserting the first anchor and the insertion of the first anchor. As seen in FIG. 5, the spinal needle 256 is placed in the knee joint capsule 252 and is viewed with the arthroscope 250 to identify a location for inserting the first anchor. The spinal needle 256 can enter through the knee joint capsule 252 above the meniscus and into the joint space. The anchor placement can then be determined a certain distance distal to this spinal needle 256 for capsular repair on the tibia. The method then involves making an incision in the knee joint structure 254 for inserting the first anchor into the knee joint structure 254. In particular, drill pin 257 (see FIG. 6) can be used to drill a hole for inserting the first anchor into the knee joint structure 254. A drill guide 258 (see FIG. 7) can be used to guide the drill pin 257. The drill guide 258 with an anchor inserted through the cannulation of the drill guide 258 is used to place the anchor into the knee joint structure 254 (see FIG. 7). The first anchor 260 (see FIG. 8) is placed in the drilled hole. The first anchor 260 is placed below the joint line 261 (see FIG. 8) and through the capsule 252 at the anterior distal portion of the capsule 252. In an example embodiment, the insertion of the first anchor is percutaneously inserting the anchor.

Figure 9:
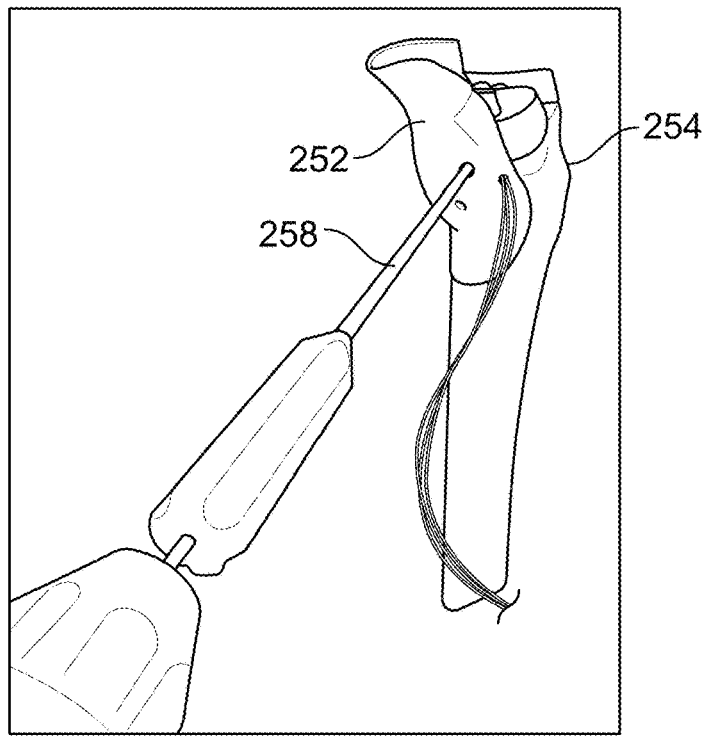
Figure 10:
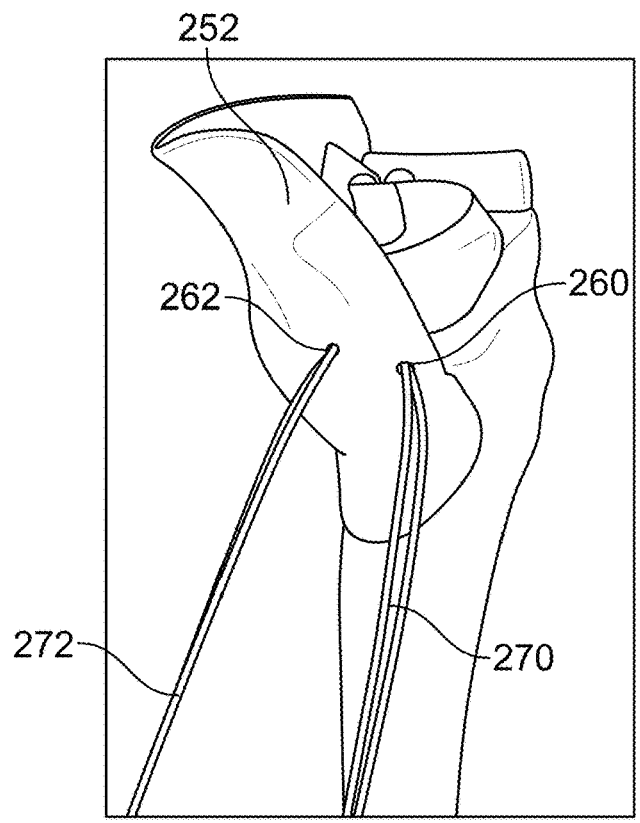
Figure 11:
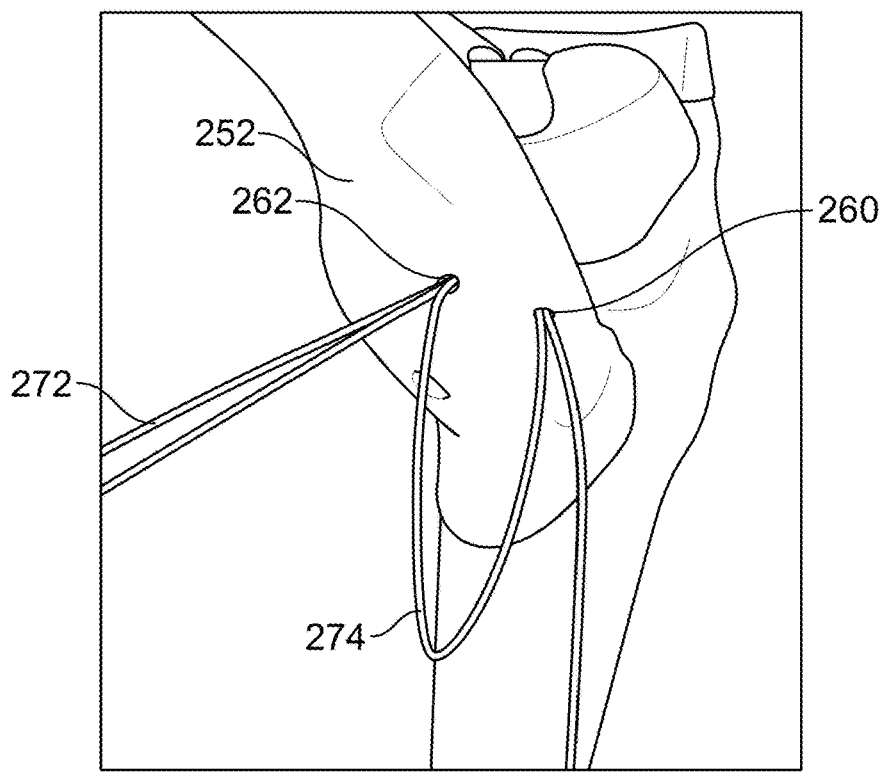
Figure 12:
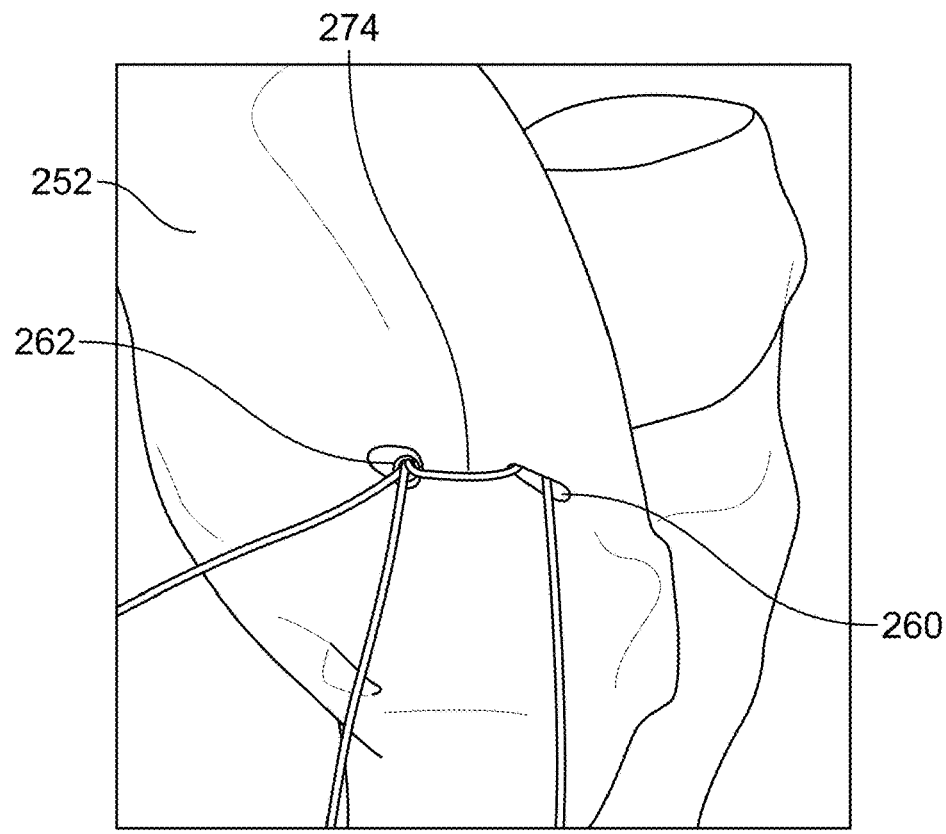
Figure 13:
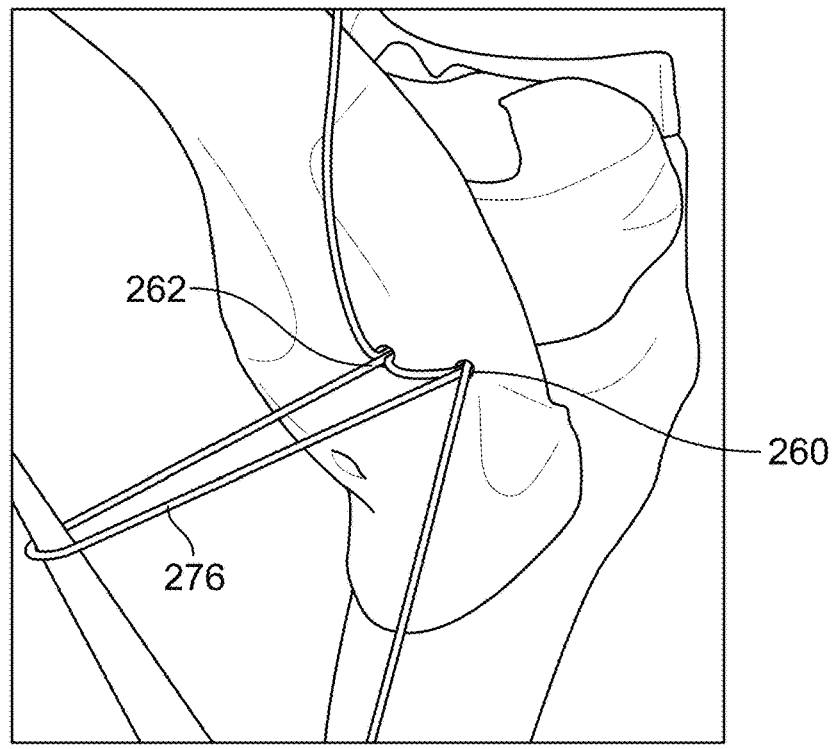
Figure 14:
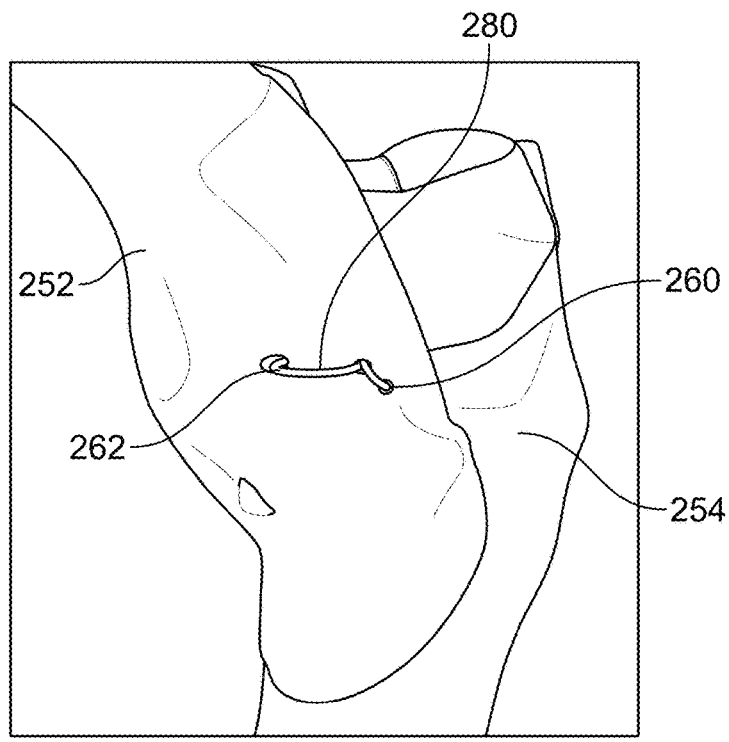

FIGS. 5 and 9 illustrate identification of the location for inserting the second anchor and insertion of the second anchor. The spinal needle 256 is placed in the knee joint 252 and is viewed with the arthroscope 250 to identify a location for inserting the second anchor. The method then involves drilling a socket in the knee joint structure 254 for inserting the second anchor. In particular, as seen in FIG. 9, drill guide 258 is used to drill a hole through the capsule 252 and into the knee joint structure 254. The second anchor 262 (see FIG. 10) is then placed in the drilled hole. In this example embodiment, the second anchor 262 is placed posterior to the first anchor 260.

In an example embodiment, the second anchor 262 is placed within about 2 cm of the first anchor. In a more particular example, the second anchor 262 is about 1 to about 2 or about 1 to about 1.5 cm from the first anchor. However, other distances between the anchors are possible as well (e.g., about 0.3, 0.4, 0.5, 0.6., 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 cm, or more (or any range between about 0.3 and 3.0 cm)).

Although in this example the spinal needle 256 is inserted multiple times and/or into multiple locations so as to determine the locations for inserting the two anchors, in other examples the spinal needle 256 could be inserted a single time and/or at a single location. The locations for inserting the one or more anchors could then be identified relative to position of the spinal needle 256. For instance, in an example embodiment, the spinal needle 256 is placed between the femur and tibia at knee joint line 261, and the arthroscope 250 is used to confirm that the spinal needle 256 is positioned at the joint line 261. The medical provider could select a distance from the knee joint line 261 at which to insert the one or more anchors through the knee joint capsule. The anchor is typically placed about 3 mm to about 5 mm below the knee joint line. The medical provider could then identify the location(s) for inserting the one or more anchors through the knee joint capsule based on the position of the spinal needle at the joint line 261. In particular, the spinal needle 256 at the joint line 261 can act as a guide for the medical provider so the medical provider is able to easily visualize precisely where the joint line is located. This will help to ensure that the medical provider places the anchors 260, 262 a desired distance below the joint line.

Embodiments of the method of repair include bridging of the anchors by any type of flexible strand (e.g., suture, suture tape, etc.) With reference to FIGS. 10-14, the method involves securing sutures from one anchor to another anchor. First anchor 260 is a suture anchor that includes sutures 270, and second anchor 262 is a suture anchor that includes sutures 272 (see FIG. 10). A suture lead 274 from first anchor 260 is fed into second anchor 262 (see FIG. 11). The suture lead 274 is then tightened between the first anchor 260 and the second anchor 262 (see FIG. 12). Suture lead 276 from the second anchor 262 is then threaded through to first anchor 260 and tightened (see FIG. 13). Securing the sutures from one anchor to another creates a bridge 280 (see FIG. 14) between the first anchor 260 and the second anchor 262. This bridge 280 functions as a band that spans capsular tissue 252 and helps to secure the capsule 252 to the knee joint structure 254. This bridge 280 also helps to prevent further meniscal extrusion.

Although the example embodiment illustrated in FIGS. 5-14 includes inserting two anchors 260, 262 to secure the knee joint capsule 252 to the knee joint structure 254, more or fewer anchors are possible. For instance, in an example embodiment, three anchors are used to secure the knee joint capsule 252 to the knee joint structure 254. In an example, the first and second suture anchors about 1 cm to about 2 cm apart, and the second and the third anchors are about 1 cm to about 2 cm apart. A suture lead from a first anchor is fed into a second anchor; suture lead from the second anchor is fed into a third anchor; and a suture lead from the third anchor is fed into the first anchor. In another example, one anchor is used to secure the knee joint capsule 252 to the knee joint structure 254. In yet another example, four or more anchors are used to secure the knee joint capsule 252 to the knee joint structure 254.

In general, the number of anchors inserted to secure the knee joint capsule 252 to the knee joint structure 254 can depend on the size of the capsular disruption. For instance, a suitable number of anchors is selected so as to cover the expanse of the tear and so that the anchors are within about 2 cm or less of one another. Typically, more anchors are selected for a larger tear than for a smaller tear. As a particular example, a common capsular disruption tear is approximately 2.5 cm. In an example, three anchors can be used for such a tear to secure the knee joint capsule 252 to the knee joint structure 254. For instance, a first anchor could be placed at or near the beginning of the tear (e.g., at the 0 cm mark), a second anchor could be placed at or near the middle of the tear (e.g., 1.25 cm mark), and a third anchor could be placed at or near the end of the tear (e.g., at the 2.5 cm mark). On the other hand, for a smaller tear, such as a 1-1.5 cm tear, one or two anchors can be inserted to secure the knee joint capsule 252 to the knee joint structure 254. Other examples are possible as well.

Furthermore, although the illustrated example involved inserting suture anchors and bridging those suture anchors together, other example anchors are possible as well. In general, any suitable tissue anchors could be used. Other example methods include other knotless anchors bridged with FiberTape® or sutureTape™, or a combination of knotted and knotless anchors and sutures. Furthermore, in some example embodiments, the tissue anchors are independent and are not bridged together.

In addition to inserting one or more anchors to secure the knee joint capsule 252 to the knee joint structure, additional steps can be taken to further treat the meniscal injury. For instance, in an example embodiment, the repair of capsular disruption can be performed concomitantly with a meniscal root repair. If the meniscal root is not torn, the capsular disruption can be repaired so the meniscus does not extrude further, and the condition does not progress to a torn meniscal root and/or the development of osteophytes. Additionally or alternatively, the repair of capsular disruption can be performed concomitantly with repair of other meniscal tears, such as a radial tear, a longitudinal tear, or an oblique tear. Furthermore, the repair of capsular disruption can be performed concomitantly with removal of osteophytes formed in the knee joint.

Additional steps can also be taken to enhance the healing environment for a meniscal injury. In an example embodiment, the method includes roughening a knee joint structure 254 to induce bleeding, so as to provide an enhanced healing environment. In an embodiment, the method includes using a rasp or like instrument to roughen medial tibial metaphysis at the level of the lesion.

In an example embodiment, the method includes augmenting the repair of the at least one of the capsular disruption or the meniscal extrusion by inserting a biological product into the knee, so as to stimulate healing of the capsular disruption and the meniscal extrusion. Any suitable biological product can be inserted to stimulate healing. For instance, in an example embodiment, the biological product is stem cells (e.g., stromal stem cells), platelet-rich plasma (PRP), a tissue graft (e.g., adipose, amnion, chorion, etc.), or combinations thereof. Other example biological products include bone marrow concentrate (BMC), bone marrow aspirate (BMA), growth factors, angiogenin, transforming growth factor-β2 (TGF-β32), tissue inhibitors of metalloproteinases (e.g., TIMP-1 and TIMP-2)), and growth factors, such as epidermal growth factor (EGF), platelet-derived growth factor (PDGF), vascular endothelial growth factor (VEGF), fibroblast growth factor (FGF), TGF-β (transforming growth factor-β), and combinations thereof. The biological product can be obtained from the patient to be treated or from another source. In an example, inserting the biological product into the knee takes place prior to (i) inserting the one or more anchors through the knee joint capsule of a knee and (ii) inserting the one or more anchors into a knee joint structure to secure the knee joint capsule to the knee joint structure. In another example, inserting the biological product into the knee takes place after (i) inserting the one or more anchors through the knee joint capsule of a knee and (ii) inserting the one or more anchors into a knee joint structure to secure the knee joint capsule to the knee joint structure.

In an embodiment, the meniscus and/or the methods described herein can be visualized using an arthroscope. The arthroscope is a diagnostic and therapeutic device utilized with minimally invasive orthopedic surgical procedures. The arthroscope provides direct visualization within the orthopedic articulating joint to assess or diagnose such anatomical structures as the meniscus, ligaments, tendons and articular surfaces.

The arthroscopist can follow a standardized approach for a complete diagnostic knee arthroscopy. In an example embodiment, a diagnostic arthroscope includes visualization of areas around the patella including the suprapatellar pouch, medial and lateral gutter, intracondylar notch, posterior medial and lateral compartments as well as the medial and lateral compartment. Each compartment has specific anatomy to investigate. This investigation can utilize an arthroscopic probe from the opposite anterior portal. The probe allows the arthroscopist to manipulate various anatomical structures to determine abnormalities to these structures.

An anterolateral portal can initially be established prior to establishing an anteromedial portal. The arthroscope and arthroscopic probe can be interchanged between either portal for maximum efficiency of the arthroscope or arthroscopic probe. Posteromedial and posterolateral portals can be established to fully appreciate the structures in the posterior aspect of the knee joint.

The meniscus can be viewed intra-articular with the arthroscope. Meniscus hyper-mobility can be assessed with the aid of an arthroscopic probe. The location of capsular disruption leading to meniscal extrusion can be appreciated through the arthroscope as well as other diagnostic tools. Utilizing the arthroscope for an intra-articular perspective of the meniscus, the medical provider can locate the beginning and ending point of extrusion that would correlate with capsular defect. In an example embodiment, the medical provider inserts a needle from the outside of the knee into the joint, verifying arthroscopically that the needle is at the starting point of meniscal extrusion/capsular disruption. The needle is used to mark the beginning and end points of the extrusion in the coronal plane (anterior to posterior aspect), and also to assess anchor placement in the transverse plane (superior and inferior aspect).

The arthroscope can also be used to verify the presence of a meniscal and/or capsular lesion. With direct arthroscopic visualization, a capsular lesion can be produced and assessed and/or evaluated for research purposes.

In addition to or alternative to visualizing the meniscus and/or methods described herein with an arthroscope, the meniscus and/or the methods described herein can be visualized using other means. For instance, in other examples, the meniscus and/or the methods described herein can be visualized using ultrasound, magnetic resonance imaging (MRI), and/or open dissection with visual inspection of the medial or lateral capsule structure with its associated bony attachment. Meniscal extrusion can be identified by palpation, visualization (e.g., ultrasound), etc. In an example, a capsular disruption and meniscal extrusion can be identified via ultrasound, MRI, etc. prior to any procedure or teaching procedure (e.g., on a cadaveric knee).

Figure 15:
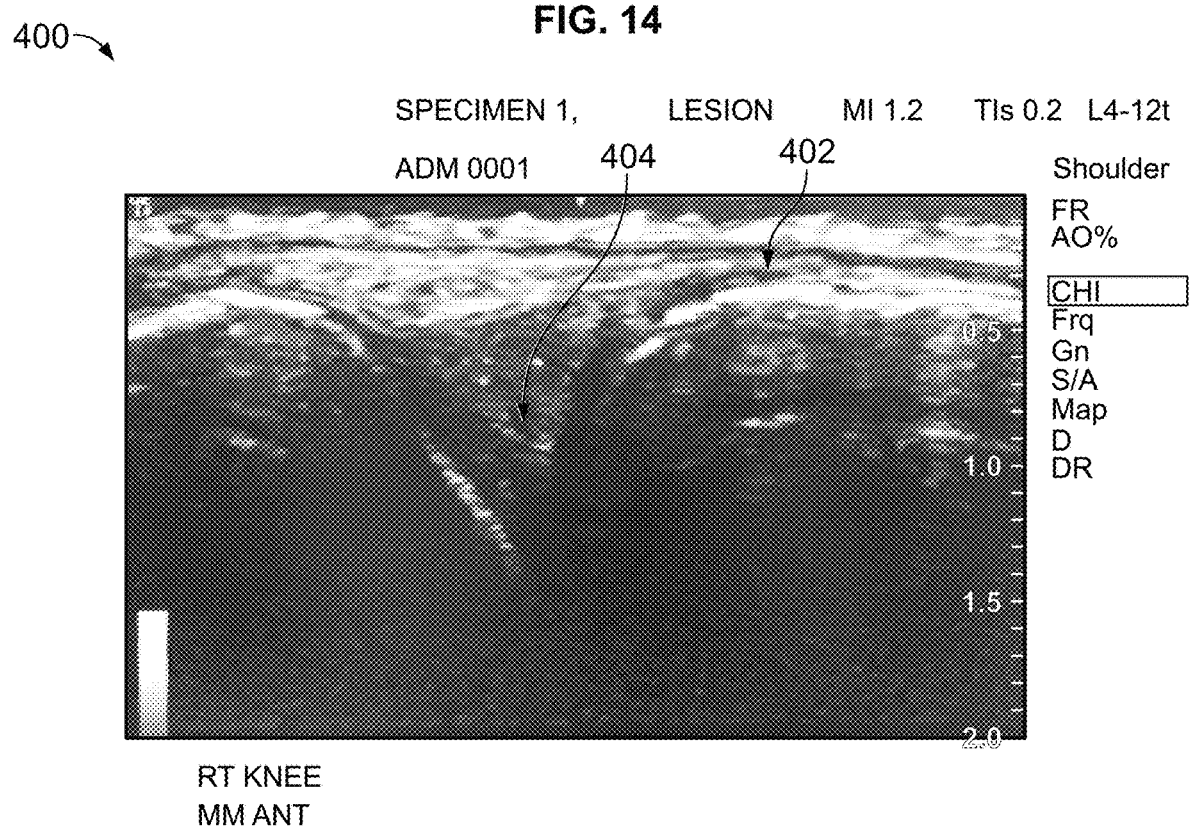
FIG. 15 illustrates an example ultrasound showing an intact capsule and an intact meniscus on a cadaveric knee, according to an example embodiment.
Figure 16:
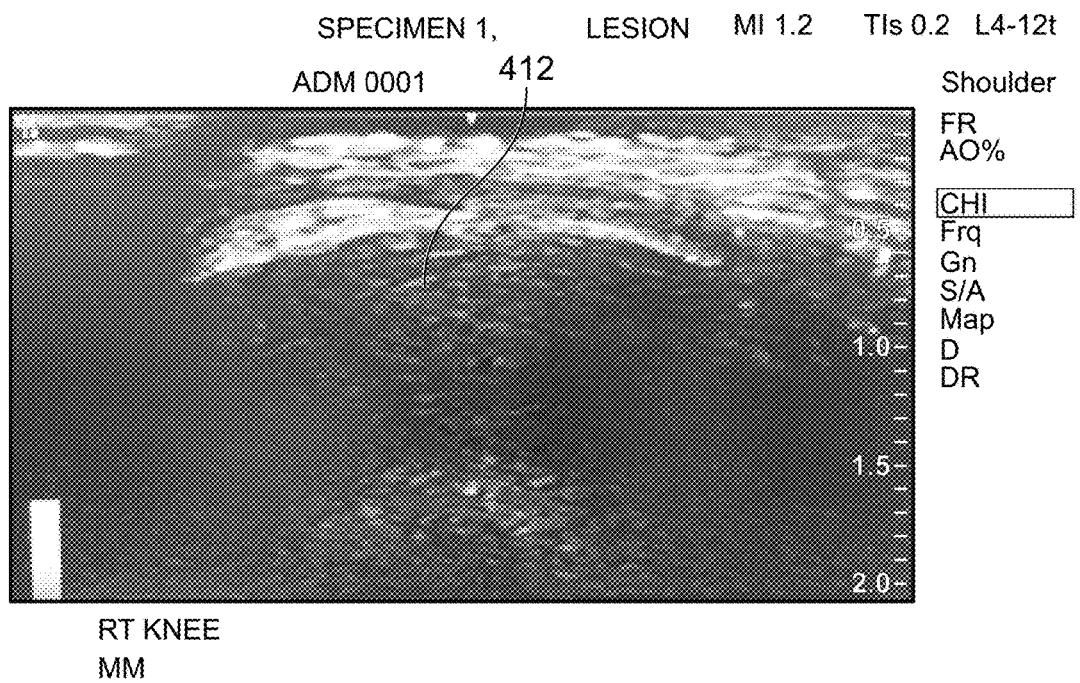
FIG. 16 illustrates an example ultrasound showing meniscal extrusion of the meniscus medially, according to an example embodiment.
Figure 17:
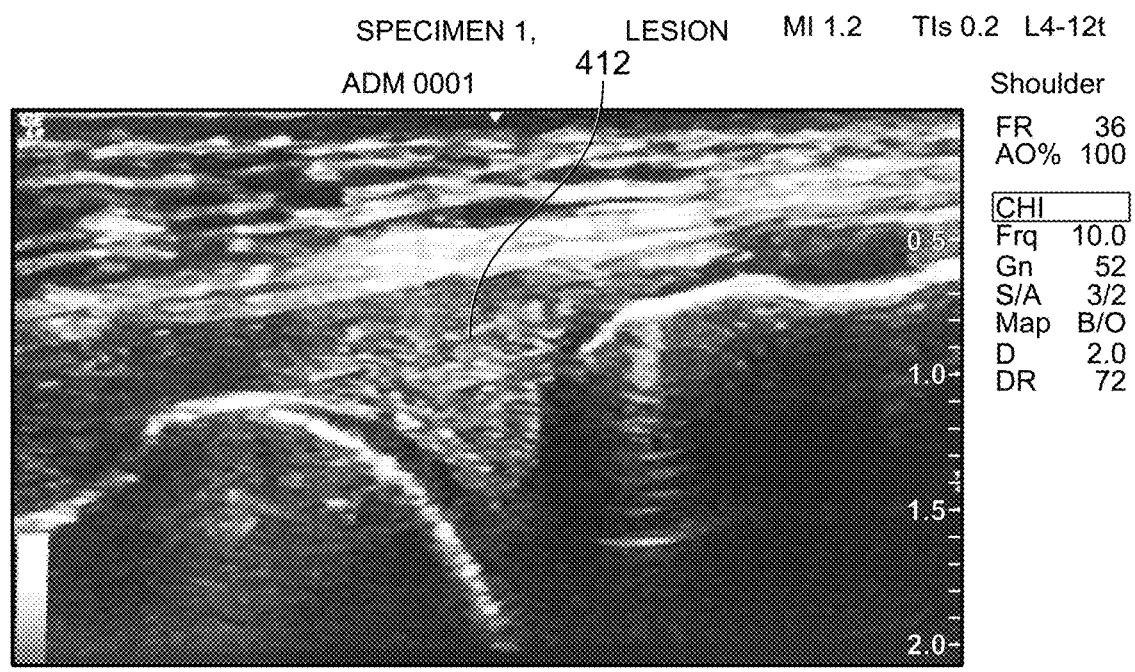
FIG. 17 illustrates an example ultrasound showing an extrusion of the meniscus medially, according to an example embodiment.

FIGS. 15-17 illustrate example ultrasounds. FIG. 15 illustrates an ultrasound 400 showing an intact capsule 402 and an intact meniscus 404 on a cadaveric knee. FIG. 16 illustrates an ultrasound 410 showing meniscal extrusion of the meniscus 412 medially. The capsule is detached from the meniscus and/or tibial periosteum. FIG. 17 illustrates another example ultrasound 420 showing further extrusion of the meniscus 412 medially. A detailed diagnosis of the meniscal extrusion can be performed using ultrasound in both a static and dynamic manner. In an example, the diagnosis involves applying a valgus moment and/or a varus moment to the knee and determining whether the meniscal extrusion is reducible based on the movement of the meniscus during the valgus and/or varus movement. Additionally or alternatively, a detailed diagnosis can be performed using ultrasound elastography (see, e.g., Drakonaki et al., *Br. J. Radiol.* 2012, 85: 1435-1445).

Also disclosed herein are methods of producing a meniscal extrusion injury in a cadaveric knee. A meniscal extrusion injury in a cadaveric knee provides a model to teach diagnosis and/or repair of meniscal extrusion. An example method for disrupting a knee joint capsule of a knee (e.g., a cadaveric knee) from a knee joint structure includes placing an instrument (e.g., a single sided banana blade scalpel) between a knee joint capsule of a knee and a knee joint structure of the knee. The example method then involves disrupting the knee joint capsule from the knee joint structure by physically elevating the instrument to force a capsular disruption.

Figure 18:
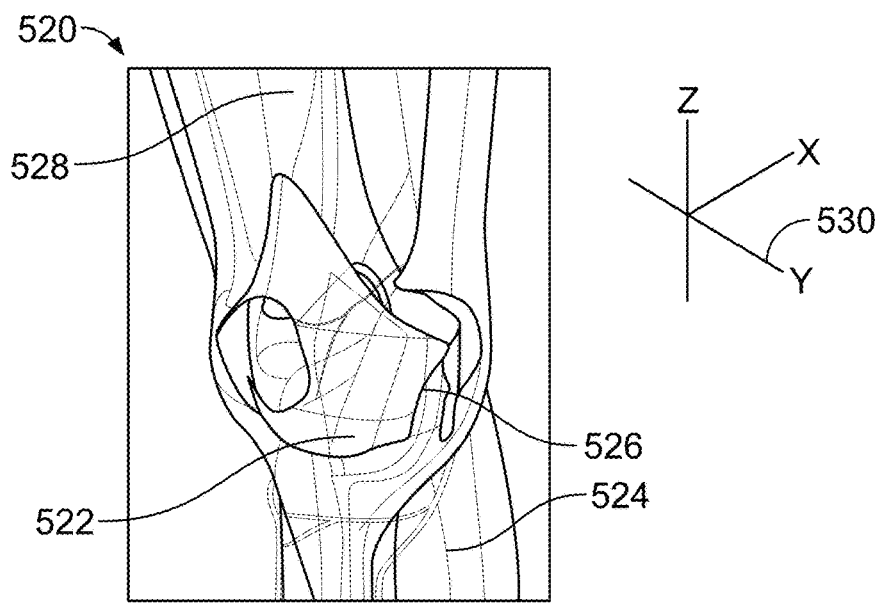
FIG. 18 illustrates an example knee, according to an example embodiment.
Figure 19:
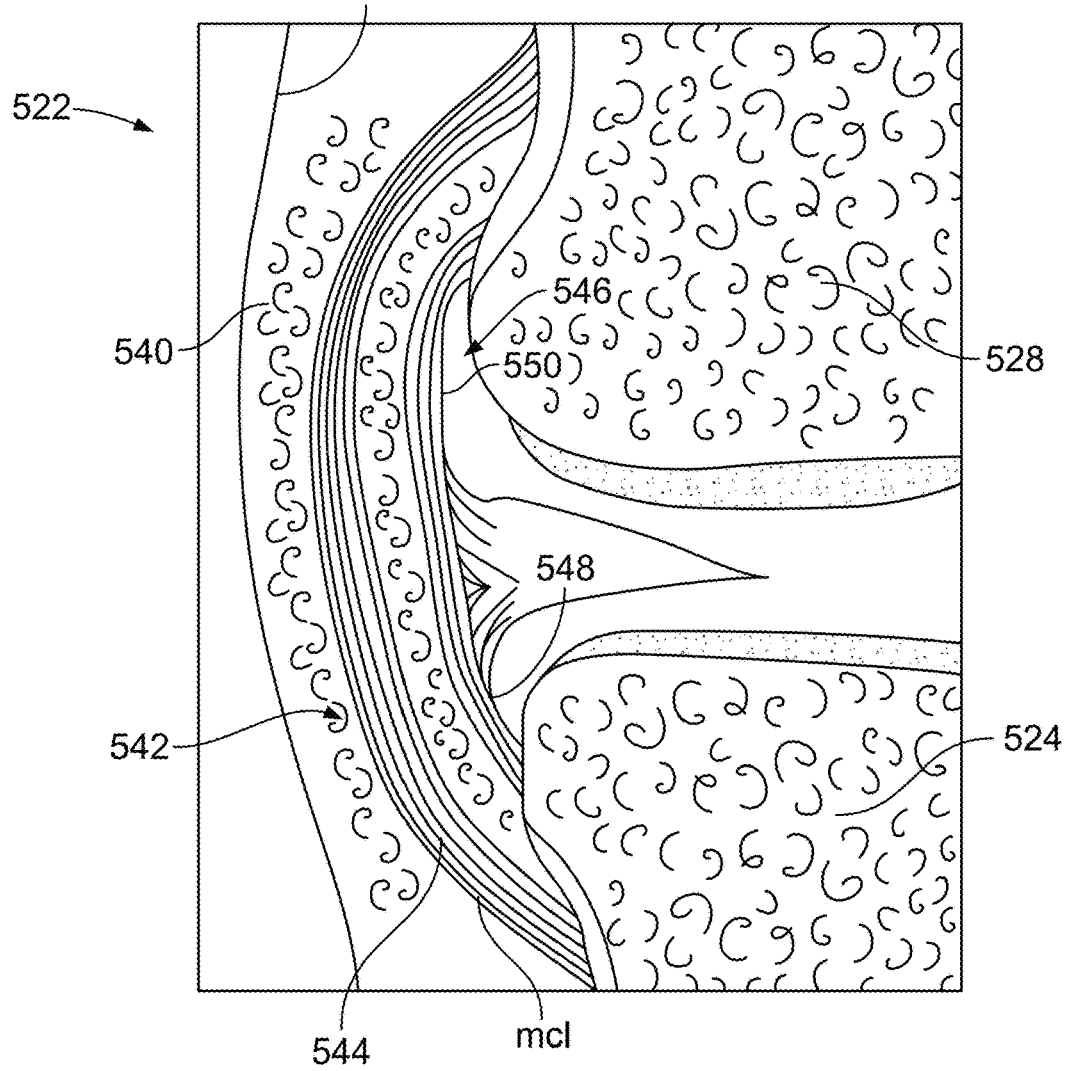
FIG. 19 illustrates a close-up, cross-sectional view of a joint capsule along the middle third of the medial side of the example knee of FIG. 18, according to an example embodiment.

This example method is described in further detail with respect to FIGS. 18-19. FIG. 18 illustrates an example knee 520 where the knee joint capsule 522 is substantially intact with the tibia 524. In an example, knee 520 is a cadaveric knee. An instrument such as a probe or a scalpel (e.g., a banana blade scalpel) is placed between the knee joint capsule 522 and tibia 524. For instance, the instrument can be placed at point 526 between the knee joint capsule 522 and tibia 524. After being placed between the knee joint capsule 522 and tibia 524, the instrument is physically elevated to force a capsular disruption. For instance, the instrument can be physically elevated along the y-axis 530. Although in this example the instrument is physically elevated along the y-axis, the instrument can be physically elevated in other directions as well. In general, the instrument can be elevated in any direction suitable to disrupt the capsule from the knee joint structure (e.g., the tibia or the femur). The extent of the forced capsular disruption can be controlled based on the force applied to physically elevate the instrument. Further, the extent of the capsular disruption can be measured by visualizing the knee with ultrasound, MRI, or other visualization mechanisms.

In an embodiment, disrupting the knee joint capsule 522 from the tibia 524 by physically elevating the instrument to force a capsular disruption comprises tearing coronary fibers of a meniscotibial ligament. FIG. 19 illustrates example coronary figures of a meniscotibial ligament. This close-up view of the medial capsule 522 illustrates the three layer structure of the medial capsule, including (i) crural fascia 540, (ii) superficial portion 542 of the MCL 544, and (iii) the deep portion 546 of the MCL 544 including meniscofemoral and meniscotibial extensions of the deep MCL. In particular, FIG. 19 illustrates coronary fibers of the meniscotibial ligament 548 and coronary fibers of the meniscofemoral ligament 550. Disrupting the knee joint capsule 522 from the tibia 524 can include tearing the coronary fibers of the meniscotibial ligament 548 from the tibia 524.

In an embodiment, meniscal extrusion occurs without any disruption or injury to the meniscus. In another embodiment, detachment of the meniscotibial ligament produces a meniscal extrusion injury in addition to or independent to the capsule disruption.

Although in the example of FIG. 18 the knee joint capsule 522 is disrupted from the tibia at a medial tibia below the joint line, the knee joint capsule 522 can be disrupted from the knee joint structure at other locations. For instance, in an example embodiment, the knee joint capsule 522 is disrupted from the knee joint structure at a lateral tibia below a knee joint line. In another example, the knee joint capsule 522 is disrupted from the knee joint structure at the femur 528. For instance, with reference to FIG. 19, disrupting the knee joint capsule from the knee joint structure can include tearing the coronary fibers of the meniscofemoral ligament 550 from the femur 528. Other examples are possible as well.

In an example embodiment, the knee 520 is used to teach a method of repairing at least one of a capsular disruption and a meniscal extrusion. In accordance with an example embodiment, an example method for teaching or practicing a method of repairing at least one of a capsular disruption and a meniscal extrusion involves providing a cadaveric knee (e.g., cadaveric knee 520) comprising at least one of a capsular disruption or a meniscal extrusion. The example method then involves using the cadaveric knee to teach a method of repairing at least one of a capsular disruption, wherein said using comprises (i) inserting one or more anchors through the knee joint capsule and (ii) inserting the one or more anchors into the knee joint structure to secure the knee joint capsule to the knee joint structure.

In an example, providing the cadaveric knee includes providing a cadaveric knee having a pre-existing capsular disruption or meniscal extrusion. Since meniscal extrusion is a common meniscal injury, many cadaveric knees can already have a pre-existing capsular disruption and meniscal extrusion. In another example, if the cadaveric knee does not have a pre-existing capsular disruption or meniscal extrusion, providing the cadaveric knee can include (i) providing a cadaveric knee having a substantially attached knee joint capsule and (ii) forcing a capsular disruption in the cadaveric knee.

In addition to being used to teach repair of a capsular disruption and meniscal extrusion, the knee 520 can also be used to teach diagnosis of a capsular disruption and meniscal extrusion. For instance, the knee 520 can be visualized with an ultrasound machine to facilitate teaching of the diagnosis. A valgus moment and/or a varus moment can be applied to the knee, and the knee can be visualized with the ultrasound during this applied moment. The capsular disruption and meniscal injury can be visualized more easily when being dynamically viewed compared to when being viewed in a static image. Therefore, dynamically visualizing the knee 520 with the ultrasound machine can help to teach diagnosing the capsular disruption and meniscal extrusion.

Disclosed herein is also a synthetic model of knee. The synthetic model of the knee can be a model to simulate capsular disruption and for a medical provider to practice repair of meniscal extrusion. In the synthetic model, a structure representing a capsule is detached from at least one of the structures representing the meniscus, the femur, and the tibia. In the synthetic model, there may or may not be a meniscal root tear as well. A synthetic model as disclosed herein is configured and adapted so that a medical provider can repair the meniscal extrusion, capsular disruption (e.g., meniscotibial ligament detachment), and/or meniscal root tear by any of the methods disclosed herein. In an embodiment, the same anchors and instrumentation that can be used to make a repair in a patient can be used to make the repair of the simulated injury in the synthetic model. The synthetic model can be a Sawbones®-like orthopedic model, whereby the model can be used, demonstrated, practiced, etc. at a table top. The synthetic model can also be a Sawbones®-like surgical model, whereby the model can simulate an arthroscopic surgery without the need for fluid. However, the model can accommodate portals and an arthroscope to better simulate surgery. In an embodiment, imaging equipment (e.g., ultrasound) can visualize an injury to the knee capsule on a synthetic model as disclosed herein.

In an embodiment, a synthetic knee model include at least part of a tibia; at least part of a femur; a detachable meniscus, wherein the meniscus can move to simulate extrusion and is also capable to tearing to simulate a meniscal lesion (e.g., a root tear); and a detachable knee capsule, including a detachable meniscotibial ligament. In an embodiment, all of these components of the knee model are synthetic. The detachable meniscus, detachable knee capsule, and detachable meniscotibial ligament can be capable of mimicking capsular disruption and meniscal extrusion, such as the capsular disruption and meniscal extrusion shown in FIGS. 1-4.

In an embodiment, a knee model includes synthetic coronary fibers attached to the meniscus and/or the bone, wherein the meniscus is intact when connected to the coronary fibers and when the fibers disconnect, the meniscus can extrude. In an embodiment, the coronary fibers are detachable and can be reattached. In an embodiment, a synthetic knee model includes a medial knee capsule where the superficial, middle, and deep layer of the thickening at the convergence of the capsule and medical collateral ligament where these layers can be visualized, even to the naked eye. In an embodiment, a synthetic knee model includes a medial knee capsule wherein a meniscotibial ligament can be visualized and repaired.

In accordance with an example embodiment, an example method to teach or practice repairing a meniscal extrusion using a synthetic model includes using a synthetic knee to teach or practice repairing the meniscal extrusion, wherein the synthetic knee comprises a synthetic knee joint capsule and a synthetic knee joint structure. The example method involves inserting one or more anchors through a synthetic knee joint capsule of a synthetic knee. The example method also involves inserting the one or more anchors into a synthetic knee joint structure to repair a capsular disruption by securing the synthetic knee joint capsule to the synthetic knee joint structure.

Knee 240 illustrated in FIGS. 5-14 is an example synthetic knee. In an example embodiment, the synthetic knee 240 includes a synthetic meniscotibial ligament with synthetic fibers, wherein the synthetic fibers are attached to a synthetic meniscus, and wherein the synthetic fibers are at least one of detached or detachable from the knee joint structure. Including such detached or detachable synthetic fibers of the meniscotibial ligament can help a medical provider to teach and/or practice diagnosis and repair of a capsular disruption and associated meniscal extrusion.

In an example, the synthetic knee is an ultrasoundable knee model that can be used to teach using an ultrasound during diagnosis and/or repair of the capsular disruption and meniscal extrusion. In such an example embodiment, the synthetic knee includes synthetic skin covering the synthetic knee joint capsule and the synthetic knee joint structure. An ultrasound machine can be used to visualize the synthetic knee joint capsule and the synthetic knee joint structure through the synthetic skin. This can help to teach diagnosis of a capsular disruption and a meniscal extrusion under more realistic conditions. This can also help to teach use of an ultrasound to confirm the successful repair of the capsular disruption and meniscal extrusion.

In an embodiment, the synthetic model is reusable, wherein a meniscal extrusion injury and repair can be performed more than once. A meniscal extrusion injury can be a capsule disruption (e.g., meniscotibial ligament detachment), and/or meniscal root tear. In an example embodiment, a reusable synthetic model includes a removable insert that includes the capsule and/or the meniscus. By including a removable insert, after performing a repair of a meniscal extrusion injury, the repaired insert can be removed and replaced with a new insert upon which another diagnosis and/or repair can be performed.

The disclosed methods described herein beneficially provide improved methods for repairing a meniscal extrusion. By repairing the underlying injury that results in the meniscal extrusion, the disclosed methods and systems of repairing a meniscal extrusion result in a more effective repair of the meniscal extrusion compared to existing repairs of meniscal extrusions. In the event that the repair of capsular disruption is performed concomitantly with a meniscal root repair, the resulting meniscal root repair will beneficially be more effective than meniscal root repairs using prior existing methods. In particular, by securing the capsule to the knee structure, the meniscal root is less likely to experience further trauma or degeneration. Similarly, in the event that the repair of capsular disruption is performed concomitantly with repair of another meniscal tear (e.g., a radial tear, a longitudinal tear, and oblique tear), the resulting meniscal tear repair is more effective than meniscal tear repairs using prior existing methods. This more effective repair of the meniscal extrusion can help to delay the early onset of osteoarthritis, further meniscal damage, and meniscal root pathology. The disclosed methods of repairing a capsular disruption and meniscal extrusion also help to reapproximate the meniscotibial (coronary) ligament fibers while thus improving mechanotransduction through the associated compartment of the knee joint.

The disclosed methods and systems also provide improved methods and systems for teaching or practicing repair of a meniscal extrusion.

In accordance with certain embodiments of the present disclosure, any of the above-described methods may be performed on a living knee (e.g. the knee of a living human or animal) or a non-living knee. The non-living knee may be a cadaveric knee or a synthetic knee, for example. The non-living knee may have or be caused to have a capsular disruption. The non-living knee may have a meniscal extrusion. The non-living knee may have a knee joint capsule and a knee joint structure, where the knee joint structure may comprise at least one of meniscus, a tibia, a femur, tibial periosteum, or femoral periosteum.

Definitions

The term "capsule disruption" or "capsular disruption" refers to a condition where the capsule is detached from the meniscus and/or bone periosteum (i.e., femoral and/or tibial). When the capsule loses this attachment to other tissue(s), the meniscus can drift from its anatomical position.

The term "meniscal extrusion" refers to the meniscus drifting from its anatomical position, where the meniscus extrudes medially or laterally.

The term "joint capsule" refers to an envelope surrounding a synovial joint, where the joint capsule includes an outer fibrous layer or membrane and an inner synovial layer or membrane. On the inside of the joint capsule, articular cartilage covers the end surfaces of the bones that articulate within that joint. The joint capsule surrounds the bones joined by the synovial joint to provide strength and lubrication.

The term "knee joint capsule" refers to an envelope that surrounds the knee joint and includes an outer fibrous layer or membrane and an inner synovial layer or membrane. The knee joint capsule surrounds the bones of the knee to provide strength and lubrication.

The term "knee joint structure" refers to the portions of the knee enveloped by and surrounding the knee joint capsule. In an example embodiment, the knee joint structure includes meniscus, the tibia, the femur, tibial periosteum, and femoral periosteum.

The term "knee joint line" refers to the line through the most distal points of the medial and lateral femoral condyles in the coronal plane, or the line through the most distal point of the femur perpendicular to the anatomical axis of the tibial shaft in the sagittal plane.

The term "meniscotibial ligament detachment" refers to the detachment of the meniscotibial ligament from the tibia and/or the meniscus. The meniscotibial ligament is also known as the coronary ligament(s) of the knee. The meniscotibial ligament is continuous and contiguous with the joint capsule and the menisci. More particularly, the meniscotibial ligament is a portion of the joint capsule which connects the inferior edges of the fibrocartilaginous menisci to the periphery of the tibial plateaus. The capsule is not removed when the ligament is stripped from its attachment at the medial tibial metaphysis. The meniscotibial ligament is a distinct structure but is not an isolated structure like the anterior collateral ligament. Rather, the meniscotibial ligament is a distinct thickening of the medial capsule, i.e., the convergence of the knee capsule and the medial collateral ligament, which attaches to the meniscus and to the tibia. The coronary fibers of the meniscotibial ligament hold the meniscus in place. The medial capsule has three layers—superficial, medial, and deep. The meniscotibial ligament forms the middle and deep layers.

The term "anterior" refers to what is in front of a subject and the term "posterior" refers to what is to the back of the subject. Furthermore, the terms "proximal" and "distal" are used to describe parts of a feature that are close to or distant from the main mass of the body of the subject, respectively.

EXAMPLES

Three example studies conducted in accordance with example embodiments of the present disclosure are described below. In particular, the first example details a study regarding medial meniscus capsular disruption, according to an example embodiment. The second example details a study regarding medial meniscus capsular repair, according to an example embodiment. The third example details a study regarding biomechanical testing to examine the effect of a medial meniscus capsular repair, according to an example embodiment.

Example 1: Medial Meniscus Capsular Disruption

A cadaveric lab was conducted to determine the possibility of creating a lesion or disruption of the anterior inferior medial capsule of the knee, often associated with meniscus extrusion pathology.

Methods

A diagnostic ultrasound of a cadaveric knee was performed, mimicking the clinical steps: first starting with the specimen in a state of relaxation, then a valgus and varus load, followed by internal and external rotation. The medial and lateral menisci were intact as confirmed by ultrasound (FIG. 17).

The anterior-middle third of the medial meniscus was located and an arthroscope was placed in a position under the meniscus to identify the intact capsular fibers of the capsule while using a probe to slightly raise the meniscus. Using a single sided banana blade scalpel angled to roughly 80 degrees, the capsule was approached from a far lateral accessory portal. Location of the banana blade was verified via ultrasound in conjunction with the arthroscope. By elevating the blade from the medial tibia below the joint line, the capsule was detached from the tibial periosteum thereby producing capsular disruption. Upon completion of the arthroscopic portion, a diagnostic ultrasound was performed as previously described.

Results

The above procedure resulted in meniscal extrusion (FIG. 18). Careful dissection of the area was completed to visualize the capsule and meniscus. The capsule was efficiently elevated from the tibia with no damage to the meniscus or capsular tissue.

Example 2: Medial Meniscus Capsular Repair

A repair of the capsule of cadaveric meniscal extrusion produced in Example 1 was completed using two knotless SutureTak® anchors. The first anchor was placed anteriorly, and the second anchor placed posterior to the first anchor. In an effort to reproduce a repair that could be completed percutaneously, the sutures associated with each anchor were carefully passed through the capsular tissue. Once this step was completed, the suture from the first anchor was loaded into the second anchor to create a suture bridge. This was repeated with the suture from the second anchor back to the first and the incision was closed.

Verification of anchor placement was possible using the arthroscope and a spinal needle. The arthroscope was positioned to allow visualization of the medial meniscus and capsule. The spinal needle was inserted through the skin on the medial side and visualized with the scope to determine if the placement was inferior to the joint line and through the capsular tissue.

A diagnostic ultrasound was performed as described previously (FIG. 19).

The ultrasound confirmed that the meniscus remained intact through the various ranges of motion and applied stresses.

Example 3: Biomechanical Testing

Cadaveric knees were tested to determine the amount of natural extrusion, to produce extrusion from an experimental lesion, and to test the effect of repairing the experimental lesion.

Sample Preparation. Six cadaveric knees were tested (3 male, 3 female, average age=60±7 years) and were prepared by potting the femoral shaft in fiberglass resin. Three samples with evidence of meniscal extrusion or joint capsule damage as examined by ultrasound were excluded from the testing. Suture tape was secured through the quadriceps tendon and reinforced with multiple medial-lateral rip stop passes of #2 sutures. A hole was drilled through the tibia and fibula, located 6.5 inches from the joint line, and a zip-tie was passed through both bones allowing for a 2.2 kg weight to be hung.

Mechanical Testing. Mechanical loading of the knee samples was performed using two E10000 Instron Electropulse Materials Testing Machines (INSTRON Corp., Canton, Mass.), with a 10 kN capacity load cells attached to the cross-head. The specimens were mounted in custom fixtures to the Instron testing surface, such that the femur was held parallel to the ground, and the knee hung at 90° flexion. Suture tape secured to the quadriceps tendon was strung through pulleys and tied off on a hook fixture suspended from the cross-head. The pulleys allowed for alignment of force vectors with the direction of cross-head movement, and also ensured that the amount of travel to extend the knee would not exceed the travel limits of the Instron machine. A load was manually applied to the suture tape which caused the knee to move into full extension. The total cross-head displacement was recorded during this single cycle load for each knee sample tested. Each sample was subjected to sinusoidal cyclic loading in position control using the displacement found in the single cycle load for amplitude at 0.2 Hz, for 100 cycles.

Sample Conditions. Each sample was loaded through 100 flexion-extension cycles and was examined via ultrasound to determine the baseline position of the medial meniscus relative to the medial aspect of the tibia. After examination, the joint capsule was detached from its attachment to the tibia, and the meniscotibial ligament was released from its insertion point. Then the knee was subjected to a second set of 100 loading cycles. The movement of the medial meniscus was determined via ultrasound, and the joint capsule was repaired using 3.0 mm knotless SutureTak® anchors (Arthrex, Inc., Naples, Fla.). After a third set of 100 cycles, the position of the medial meniscus was determined a final time for comparison to the baseline and damaged states. Ultrasound images were collected with the knee in extension, and under two conditions. First, the unloaded knee was imaged, and then a 10 Nm valgus moment was applied to the joint using a mounted force gauge and turnbuckle.

The following tables (i.e., Tables 1-6) show baseline, lesion, and repair data for the six samples for (i) Meniscus Beyond Femoral-Tibial Baseline (cm) (Pre-Cycle Resting, Pre-Cycle Varus Load, Post Cycle Resting, and Post Cycle Varus Load), (ii) Total Meniscus Length (cm) (Pre-Cycle Resting, Pre-Cycle Varus Load, Post Cycle Resting, and Post Cycle Varus Load), and (iii) Capsular Displacement from Tibial Edge (cm) (Pre-Cycle Resting, Pre-Cycle Varus Load, Post Cycle Resting, and Post Cycle Varus Load).

TABLE 1

| Donor 1 | Baseline | Lesion | Repair |
|---|---|---|---|
| Meniscus Beyond Femoral-Tibial Baseline (cm) | | | |
| Pre-Cycle Resting | 0.18 | 0.30 | 0.24 |
| Pre-Cycle Varus Load | 0.20 | 0.36 | 0.26 |
| Post Cycle Resting | 0.19 | 0.25 | 0.22 |
| Post Cycle Varus Load | 0.20 | 0.33 | 0.22 |
| Average | 0.19 | 0.31 | 0.24 |
| Total Meniscus Length (cm) | | | |
| Pre-Cycle Resting | 0.62 | 0.86 | 0.86 |
| Pre-Cycle Varus Load | 0.75 | 0.87 | 0.93 |
| Post Cycle Resting | 0.78 | 0.95 | 0.85 |
| Post Cycle Varus Load | 0.69 | 0.88 | 0.87 |
| Average | 0.71 | 0.89 | 0.88 |
| Capsular Displacement from Tibial Edge (cm) | | | |
| Pre-Cycle Resting | Not Determined (ND) | ND | 0.23 |
| Pre-Cycle Varus Load | 0.11 | 0.23 | 0.18 |
| Post Cycle Resting | ND | ND | 0.13 |
| Post Cycle Varus Load | 0.09 | 0.21 | 0.17 |
| Average | 0.05 | 0.11 | 0.18 |

TABLE 2

| Donor 2 | Baseline | Lesion | Repair |
|---|---|---|---|
| Meniscus Beyond Femoral-Tibial Baseline (cm) | | | |
| Pre-Cycle Resting | 0.16 | 0.39 | 0.28 |
| Pre-Cycle Varus Load | 0.20 | 0.41 | 0.27 |
| Post Cycle Resting | 0.23 | 0.39 | 0.27 |
| Post Cycle Varus Load | 0.26 | 0.47 | 0.27 |
| Average | 0.21 | 0.42 | 0.27 |
| Total Meniscus Length (cm) | | | |
| Pre-Cycle Resting | 0.81 | 0.88 | 0.81 |
| Pre-Cycle Varus Load | 0.89 | 0.87 | 0.88 |
| Post Cycle Resting | 0.89 | 0.86 | 0.93 |
| Post Cycle Varus Load | 0.86 | 0.88 | 0.86 |
| Average | 0.86 | 0.87 | 0.87 |
| Capsular Displacement from Tibial Edge (cm) | | | |
| Pre-Cycle Resting | 0.06 | 0.13 | 0.16 |
| Pre-Cycle Varus Load | 0.09 | 0.19 | 0.14 |
| Post Cycle Resting | ND | 0.18 | 0.13 |
| Post Cycle Varus Load | 0.08 | 0.25 | 0.07 |
| Average | 0.06 | 0.19 | 0.13 |

TABLE 3

| Donor 3 | Baseline | Lesion | Repair |
|---|---|---|---|
| Meniscus Beyond Femoral-Tibial Baseline (cm) | | | |
| Pre-Cycle Resting | 0.03 | 0.21 | 0.15 |
| Pre-Cycle Varus Load | 0.16 | 0.26 | 0.13 |
| Post Cycle Resting | 0.04 | 0.24 | 0.20 |
| Post Cycle Varus Load | 0.07 | 0.24 | 0.15 |
| Average | 0.08 | 0.24 | 0.16 |
| Total Meniscus Length (cm) | | | |
| Pre-Cycle Resting | 0.95 | 0.90 | 0.91 |
| Pre-Cycle Varus Load | 0.88 | 0.73 | 0.75 |
| Post Cycle Resting | 0.88 | 0.90 | 0.87 |
| Post Cycle Varus Load | 0.90 | 0.93 | 0.86 |
| Average | 0.90 | 0.87 | 0.85 |
| Capsular Displacement from Tibial Edge (cm) | | | |
| Pre-Cycle Resting | 0.06 | 0.13 | 0.10 |
| Pre-Cycle Varus Load | 0.06 | 0.18 | 0.11 |
| Post Cycle Resting | 0.06 | 0.23 | 0.17 |
| Post Cycle Varus Load | 0.07 | 0.17 | 0.16 |
| Average | 0.06 | 0.18 | 0.14 |

TABLE 4

| Donor 4 | Baseline | Lesion | Repair |
|---|---|---|---|
| Meniscus Beyond Femoral-Tibial Baseline (cm) | | | |
| Pre-Cycle Resting | 0.13 | 0.39 | 0.17 |
| Pre-Cycle Varus Load | 0.13 | 0.38 | 0.16 |
| Post Cycle Resting | 0.13 | 0.40 | 0.22 |
| Post Cycle Varus Load | 0.14 | 0.47 | 0.20 |
| Average | 0.13 | 0.41 | 0.19 |
| Total Meniscus Length (cm) | | | |
| Pre-Cycle Resting | 0.55 | 0.88 | 0.68 |
| Pre-Cycle Varus Load | 0.57 | 0.88 | 0.71 |
| Post Cycle Resting | 0.55 | 0.89 | 0.78 |
| Post Cycle Varus Load | 0.60 | 0.87 | 0.69 |
| Average | 0.57 | 0.88 | 0.72 |
| Capsular Displacement from Tibial Edge (cm) | | | |
| Pre-Cycle Resting | 0.14 | 0.27 | 0.12 |
| Pre-Cycle Varus Load | 0.13 | 0.30 | 0.11 |
| Post Cycle Resting | 0.12 | 0.33 | 0.16 |
| Post Cycle Varus Load | 0.12 | 0.45 | 0.09 |
| Average | 0.13 | 0.34 | 0.12 |

TABLE 5

| Donor 5 | Baseline | Lesion | Repair |
|---|---|---|---|
| Meniscus Beyond Femoral-Tibial Baseline (cm) | | | |
| Pre-Cycle Resting | 0.18 | 0.34 | 0.21 |
| Pre-Cycle Varus Load | 0.24 | 0.34 | 0.20 |

TABLE 5-continued

| Donor 5 | Baseline | Lesion | Repair |
|---|---|---|---|
| Post Cycle Resting | 0.19 | 0.24 | 0.22 |
| Post Cycle Varus Load | 0.24 | 0.31 | 0.24 |
| Average | 0.21 | 0.31 | 0.22 |
| Total Meniscus Length (cm) | | | |
| Pre-Cycle Resting | 0.94 | 0.72 | 0.68 |
| Pre-Cycle Varus Load | 0.83 | 0.88 | 0.76 |
| Post Cycle Resting | 0.93 | 0.84 | 0.82 |
| Post Cycle Varus Load | 0.73 | 0.98 | 0.75 |
| Average | 0.86 | 0.86 | 0.75 |
| Capsular Displacement from Tibial Edge (cm) | | | |
| Pre-Cycle Resting | 0.07 | 0.16 | 0.11 |
| Pre-Cycle Varus Load | 0.07 | 0.19 | 0.08 |
| Post Cycle Resting | 0.07 | 0.15 | 0.11 |
| Post Cycle Varus Load | 0.05 | 0.17 | 0.07 |
| Average | 0.07 | 0.17 | 0.09 |

TABLE 6

| Donor 6 | Baseline | Lesion | Repair |
|---|---|---|---|
| Meniscus Beyond Femoral-Tibial Baseline (cm) | | | |
| Pre-Cycle Resting | 0.06 | 0.22 | 0.20 |
| Pre-Cycle Varus Load | 0.13 | 0.29 | 0.20 |

TABLE 6-continued

| Donor 6 | Baseline | Lesion | Repair |
|---|---|---|---|
| Post Cycle Resting | 0.10 | 0.41 | 0.16 |
| Post Cycle Varus Load | 0.11 | 0.36 | 0.21 |
| Average | 0.10 | 0.32 | 0.19 |
| Total Meniscus Length (cm) | | | |
| Pre-Cycle Resting | 0.70 | 0.72 | 0.72 |
| Pre-Cycle Varus Load | 0.68 | 0.75 | 0.61 |
| Post Cycle Resting | 0.68 | 0.73 | 0.68 |
| Post Cycle Varus Load | 0.62 | 0.68 | 0.65 |
| Average | 0.67 | 0.72 | 0.67 |
| Capsular Displacement from Tibial Edge (cm) | | | |
| Pre-Cycle Resting | 0.07 | 0.18 | 0.08 |
| Pre-Cycle Varus Load | 0.07 | 0.22 | 0.11 |
| Post Cycle Resting | 0.09 | 0.31 | 0.13 |
| Post Cycle Varus Load | 0.06 | 0.27 | 0.15 |
| Average | 0.07 | 0.25 | 0.12 |

Additionally, the following tables (i.e., Tables 7-12) show averages for the baseline meniscal extrusion, the lesion meniscal extrusion, and the repair meniscal extrusion for each of the six samples. These tables also show Percent Extrusion Increase from Baseline to Lesion (%), Percent Extrusion Decrease from Lesion to Repair (%), and Percent Repair Difference from Baseline Condition (%).

TABLE 7

| | Meniscal Extrusion (as a percentage of the total length) | | | Extrusion Increase from Baseline to | Extrusion Decrease from Lesion to | Repair Difference From Baseline |
|---|---|---|---|---|---|---|
| Donor 1 | Baseline | Lesion | Repair | Lesion (%) | Repair (%) | Condition (%) |
| Averages | 27.1 | 34.8 | 26.8 | 7.7 | 8.1 | −0.3 |

TABLE 8

| | Meniscal Extrusion (as a percentage of the total length) | | | Extrusion Increase from Baseline to | Extrusion Decrease from Lesion to | Repair Difference From Baseline |
|---|---|---|---|---|---|---|
| Donor 2 | Baseline | Lesion | Repair | Lesion (%) | Repair (%) | Condition (%) |
| Averages | 24.6 | 47.6 | 31.3 | 22.9 | 16.2 | 6.7 |

TABLE 9

| | Meniscal Extrusion (as a percentage of the total length) | | | Extrusion Increase from Baseline to | Extrusion Decrease from Lesion to | Repair Difference From Baseline |
|---|---|---|---|---|---|---|
| Donor 3 | Baseline | Lesion | Repair | Lesion (%) | Repair (%) | Condition (%) |
| Averages | 8.3 | 27.5 | 18.6 | 19.1 | 8.9 | 10.3 |

TABLE 10

| Donor 4 | Meniscal Extrusion (as a percentage of the total length) | | | Extrusion Increase from Baseline to | Extrusion Decrease from Lesion to | Repair Difference From Baseline |
|---|---|---|---|---|---|---|
| | Baseline | Lesion | Repair | Lesion (%) | Repair (%) | Condition (%) |
| Averages | 23.3 | 46.6 | 26.2 | 23.2 | 20.4 | 2.9 |

TABLE 11

| Donor 5 | Meniscal Extrusion (as a percentage of the total length) | | | Extrusion Increase from Baseline to | Extrusion Decrease from Lesion to | Repair Difference From Baseline |
|---|---|---|---|---|---|---|
| | Baseline | Lesion | Repair | Lesion (%) | Repair (%) | Condition (%) |
| Averages | 24.8 | 36.0 | 28.9 | 11.2 | 7.1 | 4.1 |

TABLE 12

| Donor 6 | Meniscal Extrusion (as a percentage of the total length) | | | Extrusion Increase from Baseline to | Extrusion Decrease from Lesion to | Repair Difference From Baseline |
|---|---|---|---|---|---|---|
| | Baseline | Lesion | Repair | Lesion (%) | Repair (%) | Condition (%) |
| Averages | 14.9 | 44.4 | 28.9 | 29.5 | 15.5 | 14.0 |

These examples show that a lesion can be produced after physically disrupting an intact capsule and meniscotibial ligaments. The manually produced lesions caused instability (i.e., extrusion of the meniscus). Repairing these injuries resulted in improvement in the stability of the meniscus, although not a complete restoration of stability (i.e., full baseline of an uninjured, intact capsule and meniscus, a time zero state).

The description of the different advantageous arrangements has been presented for purposes of illustration and description, and is not intended to be exhaustive or limited to the embodiments in the form disclosed. Many modifications and variations will be apparent to those of ordinary skill in the art. Furthermore, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A method comprising:
    disrupting a knee joint capsule from a knee joint structure, wherein the knee joint structure is a cadaveric knee joint structure or a synthetic knee joint structure, by physically elevating an instrument placed between the knee joint capsule and the knee joint structure to force a capsular disruption.

2. The method of claim 1, wherein the capsular disruption comprises at least one of a tear of coronary fibers of a meniscotibial ligament or a tear of coronary fibers of a meniscofemoral ligament.

3. The method of claim 1, further comprising:
    inserting one or more anchors through the knee joint capsule at the capsular disruption; and securing the knee joint capsule to a knee joint structure to decrease a length of a meniscal extrusion, wherein securing the knee joint capsule to the knee joint structure comprises inserting the one or more anchors into the knee joint structure, wherein a knee joint structure comprises at least one of a tibia, a femur, tibial periosteum, or femoral periosteum.

4. The method of claim 3, wherein the one or more anchors comprises a suture anchor or a soft tissue anchor.

5. The method of claim 3, wherein inserting one or more anchors through the knee joint capsule comprises inserting a first anchor and a second anchor.

6. The method of claim 5, wherein the first anchor is inserted below a knee joint line and at an anterior distal portion of the knee joint capsule, and wherein the second anchor is inserted posterior to the first anchor.

7. The method of claim 5, wherein the second anchor is inserted through the knee joint capsule within about 2 cm of the first anchor.

8. The method of claim 7, wherein the second anchor is inserted through the knee joint capsule within about 1 cm to about 1.5 cm of the first anchor.

9. The method of claim 5, wherein the method further comprises securing sutures from each of the first and second anchors to the opposite anchor.

10. The method of claim 5, wherein the method further comprises securing the first anchor to the second anchor with a flexible strand.

11. The method of claim 3, wherein inserting one or more anchors through the knee joint capsule comprises percutaneously inserting the one or more anchors.

12. The method of claim 3, wherein the method further comprises drilling a hole in a bone for inserting the one or more anchors.

13. The method of claim 3, further comprising:
    visualizing a spinal needle with an arthroscope to identify a location for inserting one or more anchors through the knee joint capsule, wherein the spinal needle is inserted into the knee joint structure.

14. The method of claim 3, wherein the capsular disruption comprises the tear of coronary fibers of the meniscotibial ligament, and wherein inserting the one or more anchors into the knee joint structure comprises inserting the one or more anchors into the tibia.

\* \* \* \* \*